(12) United States Patent
Wilson

(10) Patent No.: US 11,376,304 B2
(45) Date of Patent: Jul. 5, 2022

(54) METHODS AND COMPOSITIONS FOR THE PREVENTION AND TREATMENT OF DISEASE

(71) Applicant: Stealth BioTherapeutics Inc., Needham, MA (US)

(72) Inventor: D. Travis Wilson, Newton, MA (US)

(73) Assignee: STEALTH BIOTHERAPEUTICS INC., Needham, MA (US)

( * ) Notice: Subject to any disclaimer, the term of this patent is extended or adjusted under 35 U.S.C. 154(b) by 0 days.

(21) Appl. No.: 16/994,799

(22) Filed: Aug. 17, 2020

(65) Prior Publication Data

US 2020/0376072 A1 Dec. 3, 2020

Related U.S. Application Data

(62) Division of application No. 15/504,944, filed as application No. PCT/US2015/046130 on Aug. 20, 2015, now Pat. No. 10,744,178.

(60) Provisional application No. 62/040,236, filed on Aug. 21, 2014.

(51) Int. Cl.
| | |
|---|---|
| A61K 38/07 | (2006.01) |
| A61K 45/06 | (2006.01) |
| A61K 31/192 | (2006.01) |
| A61K 31/165 | (2006.01) |
| A61P 27/02 | (2006.01) |
| A61P 13/12 | (2006.01) |
| A61K 38/18 | (2006.01) |
| A61K 38/13 | (2006.01) |
| A61K 38/06 | (2006.01) |
| A61K 31/727 | (2006.01) |
| A61K 31/737 | (2006.01) |
| A61P 7/06 | (2006.01) |
| A61P 9/12 | (2006.01) |
| A61P 29/00 | (2006.01) |

(52) U.S. Cl.
CPC ............ *A61K 38/07* (2013.01); *A61K 31/165* (2013.01); *A61K 31/192* (2013.01); *A61K 31/727* (2013.01); *A61K 31/737* (2013.01); *A61K 38/06* (2013.01); *A61K 38/13* (2013.01); *A61K 38/1875* (2013.01); *A61K 45/06* (2013.01); *A61P 7/06* (2018.01); *A61P 9/12* (2018.01); *A61P 13/12* (2018.01); *A61P 27/02* (2018.01); *A61P 29/00* (2018.01)

(58) Field of Classification Search
None
See application file for complete search history.

(56) References Cited

U.S. PATENT DOCUMENTS

| | | |
|---|---|---|
| 2009/0221514 A1 | 9/2009 | Szeto et al. |
| 2013/0059784 A1 | 3/2013 | Wilson |
| 2013/0303436 A1 | 11/2013 | Wilson |

FOREIGN PATENT DOCUMENTS

WO WO-2014/210056 A1 12/2014

OTHER PUBLICATIONS

Anonymous "COL4A3 gene" https://medlineplus.gov/genetics/gene/col4a3/ (Year: 2020).*
Anonymous "COL4A4 gene" https://medlineplus.gov/genetics/gene/col4a4/ (Year: 2020).*
Anonymous "COL4A5 gene" https://medlineplus.gov/genetics/gene/col4a5/ (Year: 2020).*
Anonymous "Treatment and Management of Alport Syndrome" https://alportsyndromenews.com/treatment-management-alport-syndrome (Year: 2019).*
Anonymous "Keratoconus" https://www.mayoclinic.org/diseases-conditions/keratoconus/diagnosis-treatment/drc-20351357 (Year: 2021).*
O'Brien F "Thin Basement Membrane Disease" Merck Manual. https://www.merckmanuals.com/professional/genitourinary-disorders/glomerular-disorders/thin-basement-membrane-disease (Year: 2020).*
Szeto H "First-in-clas cardiolipin-protective compound as a therapeutic agent to restore mitochondrial bioenergetics" British J. Pharmacol. 171:2029-2050. (Year: 2014).*
Anonymous, Alport Syndrome, National Library of Medicine Genetics Home Reference, https://ghr.nlm.nih.gov.condition/alport-syndrome (Year: 2019).
Canadian Office Action on CA 2958585 dated Sep. 2, 2021 (4 pages).
Cousins et al., "The mitochondria-targeted peptide MTP-131 prevents hydroquinone-mediated persistent injury phenotype in cultured retinal pigment epithelium cells", Investigative Ophthalmology & Visual Science, Jun. 2015, vol. 56, pp. 829.
Extended European Search Report on EP Patent Application No. 21167284.5 dated Oct. 6, 2021 (23 pages).

* cited by examiner

*Primary Examiner* — Sudhakar Katakam
*Assistant Examiner* — Zachary J Miknis
(74) *Attorney, Agent, or Firm* — Foley & Lardner LLP

(57) ABSTRACT

The present technology is directed to compositions and methods for preventing, ameliorating, or reducing the severity of one or more signs, or symptoms associated with a reduction of function, decreased expression level of, and/or deficiency in one or more of COL4A3, COL4A4 and COL4A5 genes. Also disclosed herein are methods of preventing or treating Alport Syndrome in a mammalian subject, reducing risk factors associated with Alport Syndrome, and/or reducing the likelihood or severity of Alport Syndrome. The methods comprise administering to the subject an effective amount of an aromatic-cationic peptide.

12 Claims, 10 Drawing Sheets

FIG. 1

| Stages of the Alport nephropathy | | | | |
|---|---|---|---|---|
| Stage 1 | Hematuria | | | |
| Stage 2 | | Microalbuminuria | | |
| Stage 3 | | | Proteinuria | |
| Stage 4 | | | | Declining GFR |
| Stage 5 | | | | ESRD |

Abbreviations: GFR, glomerular filtration rate; ESRD, end-stage renal disease.

# p<0.05 vs KO

\* p < 0.05 vs WT

\* p < 0.05 vs WT

METHODS AND COMPOSITIONS FOR THE PREVENTION AND TREATMENT OF DISEASE

CROSS-REFERENCE TO RELATED APPLICATIONS

This application is a divisional of U.S. patent application Ser. No. 15/504,944, filed on Feb. 17, 2017, which is a 35 U.S.C. § 371 National Phase Application of PCT/US2015/046130, filed Aug. 20, 2015, which claims the benefit of and priority to U.S. Application No. 62/040,236, filed Aug. 21, 2014, the content of which is incorporated herein by reference in their entireties.

TECHNICAL FIELD

The present technology is directed to compositions and methods for preventing, ameliorating, or reducing the severity of one or more signs, or symptoms associated with a reduction of function, decreased expression level of, and/or a deficiency in one or more of COL4A3, COL4A4 and COL4A5 genes. The present technology also relates generally to compositions and methods for preventing, ameliorating or treating Alport Syndrome and/or reducing the severity of one or more risk factors, signs, or symptoms associated with Alport Syndrome. Additionally, the present technology relates to administering an effective amount of an aromatic-cationic peptide, such as D-Arg-2',6'-Dmt-Lys-Phe-NH$_2$, to a subject suffering from or at risk for a disease or condition characterized by a reduction of function, decreased expression level of, and/or deficiency in one or more of COL4A3, COL4A4 and COL4A5 genes. In some embodiments, present technology relates to administering an effective amount of an aromatic-cationic peptide, such as D-Arg-2',6'-Dmt-Lys-Phe-NH$_2$, to a subject suffering from or at risk for Alport Syndrome.

BACKGROUND

The following description is provided to assist the understanding of the reader. None of the information provided or references cited is admitted to be prior art to the compositions and methods disclosed herein.

Alport Syndrome or hereditary nephritis is a genetic disorder characterized by glomerulonephritis, end-stage kidney disease, and hearing loss. Bloody urine (hematuria) and protein in the urine (proteinuria) are common features of this condition. Alport Syndrome can also affect the eyes causing ocular abnormalities including cataracts, lenticonus, keratoconus, as well as retinal flecks in the macula and mid periphery.

Alport Syndrome is caused by mutations in the COL4A3, COL4A4, and COL4A5 genes, which are involved in collagen biosynthesis. Mutations in any of these genes prevent the proper production or assembly of the type IV collagen alpha3-4-5 network, which is an important structural component of basement membranes in the kidney, inner ear, and eye. Basement membranes are thin, sheet-like structures that separate and support cells in many tissues. When mutations disrupt the formation of type IV collagen fibers, the basement membranes of the kidneys are incapable of filtering waste products from the blood and facilitating normal urine production, thereby resulting in the release of blood and protein into the urine. The abnormalities of type IV collagen in kidney basement membranes cause gradual scarring of the kidneys, eventually leading to end-stage renal disease (ESRD). Progression of the disease leads to basement membrane thickening and gives a "basket-weave" appearance from splitting of the glomerular basement membrane (GBM), specifically the lamina densa layer. The accumulation of extracellular matrix in the GBM and the mesangium as a function of renal disease progression is a feature shared by a variety of glomerular diseases including Alport Syndrome.

Patients with Alport Syndrome frequently develop sensorineural hearing loss/deafness, which is caused by abnormalities of the inner ear, during late childhood or early adolescence. Affected individuals may also have misshapen lenses in the eyes (anterior lenticonus) and abnormal coloration of the light-sensitive tissue of the retina. These eye abnormalities seldom lead to vision loss. Significant hearing loss, eye abnormalities, and progressive kidney disease are more common in males with Alport Syndrome than in affected females.

As there is no known cure for the condition, treatments are mostly geared towards providing symptomatic relief. Proteinuria is often treated with ACE inhibitors. Once kidney failure has developed, patients attempt to manage their condition with dialysis or surgery.

SUMMARY

In one aspect, the present disclosure provides methods for treating or preventing Alport Syndrome, and/or treating or preventing the signs or symptoms of Alport Syndrome in a subject in need thereof by administering to the subject a therapeutically effective amount of an aromatic-cationic peptide such as D-Arg-2',6'-Dmt-Lys-Phe-NH$_2$ or a pharmaceutically acceptable salt thereof, thereby resulting in the prevention or treatment of one or more signs or symptoms of Alport Syndrome. In some embodiments of the methods of the present technology, the pharmaceutically acceptable salt comprises acetate, tartrate, or trifluoroacetate salt.

In some embodiments of the methods of the present technology, the signs or symptoms of Alport Syndrome include one or more of hematuria, proteinuria, cylindruria, leukocyturia, hypertension, edema, microalbuminuria, declining glomerular filtration rate, interstitial fibrosis, interstitial inflammation, tubular damage, GBM ultrastructural abnormalities, nephrotic syndrome, glomerulonephritis, end-stage kidney disease, chronic anemia, macrothrombocytopenia, osteodystrophy, sensorineural deafness, anterior lenticonus, dot-and-fleck retinopathy, posterior polymorphous corneal dystrophy, recurrent corneal erosion, temporal macular thinning, cataracts, lacrimation, photophobia, vision loss, keratoconus, and leiomyomatosis.

In some embodiments of the methods of the present technology, the subject displays reduced expression of the alpha-5 chain of type IV collagen compared to a normal control subject. In some embodiments of the methods of the present technology, the subject displays reduced expression of the alpha-4 chain of type IV collagen compared to a normal control subject. In some embodiments of the methods of the present technology, the subject displays reduced expression of the alpha-3 chain of type IV collagen compared to a normal control subject. In some embodiments of the methods of the present technology, the subject displays reduced expression of the alpha-3 and alpha-4 chains of type IV collagen compared to a normal control subject. In some embodiments of the methods of the present technology, the subject displays reduced expression of the alpha-3 and alpha-5 chains of type IV collagen compared to a normal control subject. In some embodiments of the methods of the present technology, the subject displays reduced expression of the alpha-4 and alpha-5 chains of type IV collagen compared to a normal control subject. In some embodiments of the methods of the present technology, the subject displays reduced expression of the alpha-3, alpha-4, and alpha-5 chains of type IV collagen compared to a normal control subject.

In some embodiments of the methods of the present technology, the subject shows persistent expression of fetal-specific alpha-1 and alpha-2 isoforms of type IV collagen.

In some embodiments of the methods of the present technology, the subject displays aberrant levels and/or function of one or more of ADAM8, fibronectin, myosin 10, MMP-2, MMP-9, and podocin compared to a normal control subject. In certain embodiments of the methods of the present technology, peptide treatment restores levels and/or function of said proteins.

In some embodiments of the methods of the present technology, the subject has been diagnosed as having Alport Syndrome. In some embodiments of the methods of the present technology, the subject is diagnosed with X-linked Alport Syndrome, autosomal dominant Alport Syndrome or autosomal recessive Alport Syndrome. In some embodiments of the methods of the present technology, the subject is diagnosed with X-linked juvenile Alport Syndrome with deafness. In other embodiments of the methods of the present technology, the subject is diagnosed with X-linked adult Alport Syndrome with deafness. In some embodiments of the methods of the present technology, the subject is diagnosed with X-linked adult Alport Syndrome without deafness or other non-renal defects.

In certain embodiments of the methods of the present technology, the subject carries a genetic mutation in one or more of COL4A3, COL4A4, and COL4A5. In some embodiments of the methods of the present technology, the subject is human.

In some embodiments of the methods of the present technology, the aromatic-cationic peptide is administered orally, topically, intranasally, systemically, intravenously, subcutaneously, intraperitoneally, intradermally, intraocularly, iontophoretically, transmucosally, or intramuscularly.

In some embodiments of the methods of the present technology, the aromatic-cationic peptide is administered daily for 1 week or more. In some embodiments of the methods of the present technology, the aromatic-cationic peptide is administered daily for 2 weeks or more. In some embodiments of the methods of the present technology, the aromatic-cationic peptide is administered daily for 3 weeks or more. In some embodiments of the methods of the present technology, the aromatic-cationic peptide is administered daily for 4 weeks or more. In some embodiments of the methods of the present technology, the aromatic-cationic peptide is administered daily for 6 weeks or more. In some embodiments of the methods of the present technology, the aromatic-cationic peptide is administered daily for 12 weeks or more.

In some embodiments, in addition to administration of aromatic-cationic peptides, the method further comprises separately, sequentially or simultaneously administering one or more additional therapeutic agents to the subject, wherein the additional therapeutic agents are selected from the group consisting of: angiotensin II converting enzyme inhibitors (ACE inhibitors), angiotensin II receptor blockers (ARBs), HMG-CoA reductase inhibitors, aldosterone inhibitors, aliskiren, calcineurin inhibitors (e.g., cyclosporine A, tacrolimus), endothelin receptor antagonists (e.g., sitaxentan, ambrisentan (LETAIRIS), atrasentan, BQ-123, zibotentan, bosentan (TRACLEER), macitentan, tezosentan, BQ-788 and A192621), sulodexide, vasopeptidase inhibitors (e.g., AVE7688), anti-transforming growth factor-β1 antibody, chemokine receptor 1 blockers, bone morphogenetic protein-7, PPARγ agonists (e.g., rosiglitazone, pioglitazone, MRL24, Fmoc-L-Leu, SR1664, SR1824, GW0072, MCC555, CLX-0921, PAT5A, L-764406, nTZDpa, CDDO (2-cyano-3,12-dioxooleana-1,9-dien-28-oic acid), ragaglitazar, O-arylmandelic acids, and NSAIDs) and BAY-12-9566.

In some embodiments, in addition to administration of aromatic-cationic peptides, the method also includes separately, sequentially or simultaneously administering to the subject one or more ACE inhibitors (angiotensin II converting enzyme inhibitors) selected from the group consisting of captopril, alacepril, lisinopril, imidapril, quinapril, temocapril, delapril, benazepril, cilazapril, trandolapril, enalapril, ceronapril, fosinopril, imadapril, mobertpril, perindopril, ramipril, spirapril, randolapril and pharmaceutically acceptable salts of such compounds. In some embodiments of the methods of the present technology, there is a synergistic effect between the aromatic-cationic peptide and the ACE inhibitors with respect to the prevention or treatment of Alport Syndrome.

In some embodiments, in addition to administration of aromatic-cationic peptides, the method also includes separately, sequentially or simultaneously administering to the subject one or more ARBs (angiotensin II receptor blockers) selected from the group consisting of losartan, candesartan, valsartan, eprosartan, telmisartan, and irbesartan. In some embodiments of the methods of the present technology, there is a synergistic effect between the aromatic-cationic peptide and the ARBs with respect to the prevention or treatment of Alport Syndrome.

In some embodiments, in addition to administration of aromatic-cationic peptides, the method also includes separately, sequentially or simultaneously administering to the subject one or more HMG-CoA reductase inhibitors (or statins) selected from the group consisting of lovastatin (e.g., ADVICOR® (niacin extended-release/lovastatin) (AbbVie Pharmaceuticals, Chicago, Ill.), ALTOPREV™ (lovastatin extended-release) (Shiongi, Inc., Atlanta, Ga.), MEVACOR® (Merck, Whitehouse Station, N.J.), atorvastatin (e.g., CADUET® (amlodipine and atorvastatin) (Pfizer, Morrisville, Pa.), LIPITOR® (Pfizer, Morrisville, Pa.)), rosuvastatin and/or rosuvastatin calcium (e.g., CRESTOR® (AstraZeneca, London, England)), simvastatin (e.g., JUVISYNC® (sitagliptin/simvastatin) (Merck, Whitehouse Station, N.J.)), SIMCOR® (niacin extended-release/simvastatin) (AbbVie Pharmaceuticals, Chicago, Ill.), VYTORIN® (ezetimibe/simvastatin) (Merck, Whitehouse Station, N.J.), and ZOCOR® (Merck, Whitehouse Station, N.J.)), fluvastatin and/or fluvastatin sodium (e.g., LESCOL®, LESCOL XL (fluvastatin extended-release) (Mylan Pharmaceuticals, Morgantown, W. Va.)), pitavastatin (e.g., LIVALO® (Kowa Pharmaceuticals, Montgomery, Ala.)), pravastatin and/or pravastatin sodium (e.g., PRAVACHOL® (Bristol-Myers Squibb, New York, N.Y.)). In some embodiments of the methods of the present technology, there is a synergistic effect between the aromatic-cationic peptide and the HMG-CoA reductase inhibitors with respect to the prevention or treatment of Alport Syndrome.

In some embodiments, in addition to administration of aromatic-cationic peptides, the method also includes separately, sequentially or simultaneously administering to the subject one or more aldosterone inhibitors selected from the group consisting of spironolactone (Aldactone®), eplerenone (Inspra®), canrenone (canrenoate potassium), prorenone (prorenoate potassium), and mexrenone (mexrenoate potassium). In some embodiments of the methods of the present technology, there is a synergistic effect between the aromatic-cationic peptide and the aldosterone inhibitors with respect to the prevention or treatment of Alport Syndrome.

In some embodiments, in addition to administration of aromatic-cationic peptides, the method also includes separately, sequentially or simultaneously administering to the subject the matrix metalloproteinase inhibitor BAY-12-9566. In some embodiments of the methods of the present technology, there is a synergistic effect between the aromatic-cationic peptide and BAY-12-9566 with respect to the prevention or treatment of Alport Syndrome.

Additionally or alternatively, in some embodiments of the method, peptide treatment results in elevated Mfn1 expression and/or function compared to an untreated Alport Syndrome subject.

In one aspect, the present technology provides a method for reducing progressive glomerulonephritis characterized by mesangial matrix expansion and GBM irregularities in a mammalian subject having or suspected of having Alport Syndrome, the method comprising: administering to the subject a therapeutically effective amount of the aromatic-cationic peptide D-Arg-2',6'-Dmt-Lys-Phe-NH$_2$ or a pharmaceutically acceptable salt thereof. In some embodiments of the methods of the present technology, the pharmaceutically acceptable salt comprises acetate, tartrate, or trifluoroacetate salt.

In some embodiments of the methods of the present technology, the mammalian subject has decreased expression of one or more of COL4A3, COL4A4, or COL4A5 compared to a normal control subject.

In some embodiments of the methods of the present technology, the mammalian subject has increased expression of MMP-9 in mesangial cells compared to a normal control subject. In some embodiments of the methods of the present technology, the mammalian subject has altered urine levels of one or more of ADAM8, fibronectin, myosin 10, MMP-2, and podocin compared to a normal control subject.

In some embodiments of the methods of the present technology, a combination of three urine biomarkers is altered in the mammalian subject compared to a normal control subject. In one particular embodiment, the mammalian subject has altered urine levels of fibronectin, myosin 10, and MMP-2 compared to a normal control subject. In another embodiment, the mammalian subject has altered urine levels of fibronectin, myosin 10, and MMP-9 compared to a normal control subject.

In other embodiments of the methods of the present technology, a combination of two urine biomarkers is altered in the mammalian subject compared to a normal control subject. In one particular embodiment, the mammalian subject has altered urine levels of myosin 10 and MMP-2 compared to a normal control subject. In another embodiment, the mammalian subject has altered urine levels of myosin 10 and MMP-9 compared to a normal control subject. In some embodiments of the methods of the present technology, the subject is human.

Additionally or alternatively, in some embodiments of the method, peptide treatment results in elevated Mfn1 expression and/or function compared to an untreated Alport Syndrome subject.

In some embodiments of the methods of the present technology, the aromatic-cationic peptide is administered orally, topically, intranasally, systemically, intravenously, subcutaneously, intraperitoneally, intradermally, intraocularly, iontophoretically, transmucosally, or intramuscularly.

In some embodiments of the methods of the present technology, the aromatic-cationic peptide is administered daily for 1 week or more. In some embodiments of the methods of the present technology, the aromatic-cationic peptide is administered daily for 2 weeks or more. In some embodiments of the methods of the present technology, the aromatic-cationic peptide is administered daily for 3 weeks or more. In some embodiments of the methods of the present technology, the aromatic-cationic peptide is administered daily for 4 weeks or more. In some embodiments of the methods of the present technology, the aromatic-cationic peptide is administered daily for 6 weeks or more. In some embodiments of the methods of the present technology, the aromatic-cationic peptide is administered daily for 12 weeks or more.

In some embodiments, in addition to administration of aromatic-cationic peptides, the method also includes separately, sequentially or simultaneously administering to the subject one or more ACE inhibitors (angiotensin II converting enzyme inhibitors) selected from the group consisting of captopril, alacepril, lisinopril, imidapril, quinapril, temocapril, delapril, benazepril, cilazapril, trandolapril, enalapril, ceronapril, fosinopril, imadapril, mobertpril, perindopril, ramipril, spirapril, randolapril and pharmaceutically acceptable salts of such compounds. In some embodiments of the methods of the present technology, the combination of the aromatic-cationic peptide and the ACE inhibitor has a synergistic effect in the reduction of progressive glomerulonephritis.

In some embodiments, in addition to administration of aromatic-cationic peptides, the method also includes separately, sequentially or simultaneously administering to the subject one or more ARBs (angiotensin II receptor blockers) selected from the group consisting of losartan, candesartan, valsartan, eprosartan, telmisartan, and irbesartan. In some embodiments of the methods of the present technology, the combination of the aromatic-cationic peptide and the ARB has a synergistic effect in the reduction of progressive glomerulonephritis.

In some embodiments, in addition to administration of aromatic-cationic peptides, the method also includes separately, sequentially or simultaneously administering to the subject one or more HMG-CoA reductase inhibitors (or statins) selected from the group consisting of lovastatin (e.g., ADVICOR® (niacin extended-release/lovastatin) (AbbVie Pharmaceuticals, Chicago, Ill.), ALTOPREV™ (lovastatin extended-release) (Shiongi, Inc., Atlanta, Ga.), MEVACOR® (Merck, Whitehouse Station, N.J.), atorvastatin (e.g., CADUET® (amlodipine and atorvastatin) (Pfizer, Morrisville, Pa.), LIPITOR® (Pfizer, Morrisville, Pa.)), rosuvastatin and/or rosuvastatin calcium (e.g., CRESTOR® (AstraZeneca, London, England)), simvastatin (e.g., JUVISYNC® (sitagliptin/simvastatin) (Merck, Whitehouse Station, N.J.)), SIMCOR® (niacin extended-release/simvastatin) (AbbVie Pharmaceuticals, Chicago, Ill.), VYTORIN® (ezetimibe/simvastatin) (Merck, Whitehouse Station, N.J.), and ZOCOR® (Merck, Whitehouse Station, N.J.)), fluvastatin and/or fluvastatin sodium (e.g., LESCOL®, LESCOL XL (fluvastatin extended-release) (Mylan Pharmaceuticals, Morgantown, W. Va.)), pitavastatin (e.g., LIVALO® (Kowa Pharmaceuticals, Montgomery, Ala.)), pravastatin and/or pravastatin sodium (e.g., PRAVACHOL® (Bristol-Myers Squibb, New York, N.Y.)). In some embodiments of the methods of the present technology, the combination of the aromatic-cationic peptide and the HMG-CoA reductase inhibitor has a synergistic effect in the reduction of progressive glomerulonephritis.

In some embodiments, in addition to administration of aromatic-cationic peptides, the method also includes separately, sequentially or simultaneously administering to the subject one or more aldosterone inhibitors selected from the group consisting of spironolactone (Aldactone®), eplerenone (Inspra®), canrenone (canrenoate potassium), prorenone (prorenoate potassium), and mexrenone (mexrenoate potassium). In some embodiments of the methods of the present technology, the combination of the aromatic-cationic peptide and the aldosterone inhibitor has a synergistic effect in the reduction of progressive glomerulonephritis.

In some embodiments, in addition to administration of aromatic-cationic peptides, the method also includes separately, sequentially or simultaneously administering to the subject the matrix metalloproteinase inhibitor BAY-12-9566. In some embodiments of the methods of the present technology, the combination of the aromatic-cationic peptide and BAY-12-9566 has a synergistic effect in the reduction of progressive glomerulonephritis.

In one aspect, the present technology provides for methods for reducing the risk, signs or symptoms of Alport Syndrome in a mammalian subject having decreased expression of COL4A3, COL4A4, or COL4A5 compared to a normal control subject. In some embodiments, the method includes administering to the subject a therapeutically effective amount of the aromatic-cationic peptide D-Arg-2',6'-Dmt-Lys-Phe-NH$_2$ or a pharmaceutically acceptable salt thereof, thereby resulting in the prevention or delay of onset of one or more risks, signs or symptoms of Alport Syndrome. In some embodiments of the methods of the present technology, the pharmaceutically acceptable salt comprises acetate, tartrate, or trifluoroacetate salt.

In some embodiments of the methods of the present technology, the signs or symptoms of Alport Syndrome include one or more of hematuria, proteinuria, cylindruria, leukocyturia, hypertension, edema, microalbuminuria, declining glomerular filtration rate, interstitial fibrosis, interstitial inflammation, tubular damage, GBM ultrastructural abnormalities, nephrotic syndrome, glomerulonephritis, end-stage kidney disease, chronic anemia, macrothrombocytopenia, osteodystrophy, sensorineural deafness, anterior lenticonus, dot-and-fleck retinopathy, posterior polymorphous corneal dystrophy, recurrent corneal erosion, temporal macular thinning, cataracts, lacrimation, photophobia, vision loss, keratoconus, and leiomyomatosis.

In certain embodiments of the methods of the present technology, the subject carries a genetic mutation in one or more of COL4A3, COL4A4, and COL4A5. In some embodiments of the methods of the present technology, the subject is human.

Additionally or alternatively, in some embodiments of the method, peptide treatment results in elevated Mfn1 expression and/or function compared to an untreated Alport Syndrome subject.

In some embodiments of the methods of the present technology, the aromatic-cationic peptide is administered orally, topically, intranasally, systemically, intravenously, subcutaneously, intraperitoneally, intradermally, intraocularly, iontophoretically, transmucosally, or intramuscularly.

In some embodiments of the methods of the present technology, the aromatic-cationic peptide is administered daily for 1 week or more. In some embodiments of the methods of the present technology, the aromatic-cationic peptide is administered daily for 2 weeks or more. In some embodiments of the methods of the present technology, the aromatic-cationic peptide is administered daily for 3 weeks or more. In some embodiments of the methods of the present technology, the aromatic-cationic peptide is administered daily for 4 weeks or more. In some embodiments of the methods of the present technology, the aromatic-cationic peptide is administered daily for 6 weeks or more. In some embodiments of the methods of the present technology, the aromatic-cationic peptide is administered daily for 12 weeks or more.

In some embodiments, in addition to administration of aromatic-cationic peptides, the method further comprises separately, sequentially or simultaneously administering one or more additional therapeutic agents to the subject, wherein the additional therapeutic agents are selected from the group consisting of: angiotensin II converting enzyme inhibitors (ACE inhibitors), angiotensin II receptor blockers (ARBs), HMG-CoA reductase inhibitors, aldosterone inhibitors, aliskiren, calcineurin inhibitors (e.g., cyclosporine A, tacrolimus), endothelin receptor antagonists (e.g., sitaxentan, ambrisentan (LETAIRIS), atrasentan, BQ-123, zibotentan, bosentan (TRACLEER), macitentan, tezosentan, BQ-788 and A192621), sulodexide, vasopeptidase inhibitors (e.g., AVE7688), anti-transforming growth factor-β1 antibody, chemokine receptor 1 blockers, bone morphogenetic protein-7, PPARγ agonists (e.g., rosiglitazone, pioglitazone, MRL24, Fmoc-L-Leu, SR1664, SR1824, GW0072, MCC555, CLX-0921, PAT5A, L-764406, nTZDpa, CDDO (2-cyano-3,12-dioxooleana-1,9-dien-28-oic acid), ragaglitazar, O-arylmandelic acids, and NSAIDs) and BAY-12-9566.

In some embodiments, in addition to administration of aromatic-cationic peptides, the method also includes separately, sequentially or simultaneously administering to the subject one or more ACE inhibitors (angiotensin II converting enzyme inhibitors) selected from the group consisting of captopril, alacepril, lisinopril, imidapril, quinapril, temocapril, delapril, benazepril, cilazapril, trandolapril, enalapril, ceronapril, fosinopril, imadapril, mobertpril, perindopril, ramipril, spirapril, randolapril and pharmaceutically acceptable salts of such compounds. In some embodiments of the methods of the present technology, there is a synergistic effect between the aromatic-cationic peptide and the ACE inhibitors with respect to reducing the risk, signs or symptoms of Alport Syndrome.

In some embodiments, in addition to administration of aromatic-cationic peptides, the method also includes separately, sequentially or simultaneously administering to the subject one or more ARBs (angiotensin II receptor blockers) selected from the group consisting of losartan, candesartan, valsartan, eprosartan, telmisartan, and irbesartan. In some embodiments of the methods of the present technology, there is a synergistic effect between the aromatic-cationic peptide and the ARBs with respect to reducing the risk, signs or symptoms of Alport Syndrome.

In some embodiments, in addition to administration of aromatic-cationic peptides, the method also includes separately, sequentially or simultaneously administering to the subject one or more HMG-CoA reductase inhibitors (or statins) selected from the group consisting of lovastatin (e.g., ADVICOR® (niacin extended-release/lovastatin) (AbbVie Pharmaceuticals, Chicago, Ill.), ALTOPREV™ (lovastatin extended-release) (Shiongi, Inc., Atlanta, Ga.), MEVACOR® (Merck, Whitehouse Station, N.J.), atorvastatin (e.g., CADUET® (amlodipine and atorvastatin) (Pfizer, Morrisville, Pa.), LIPITOR® (Pfizer, Morrisville, Pa.)), rosuvastatin and/or rosuvastatin calcium (e.g., CRESTOR®

(AstraZeneca, London, England)), simvastatin (e.g., JUVISYNC® (sitagliptin/simvastatin) (Merck, Whitehouse Station, N.J.)), SIMCOR® (niacin extended-release/simvastatin) (AbbVie Pharmaceuticals, Chicago, Ill.), VYTORIN® (ezetimibe/simvastatin) (Merck, Whitehouse Station, N.J.), and ZOCOR® (Merck, Whitehouse Station, N.J.)), fluvastatin and/or fluvastatin sodium (e.g., LESCOL®, LESCOL XL (fluvastatin extended-release) (Mylan Pharmaceuticals, Morgantown, W. Va.)), pitavastatin (e.g., LIVALO® (Kowa Pharmaceuticals, Montgomery, Ala.)), pravastatin and/or pravastatin sodium (e.g., PRAVACHOL® (Bristol-Myers Squibb, New York, N.Y.)). In some embodiments of the methods of the present technology, there is a synergistic effect between the aromatic-cationic peptide and the HMG-CoA reductase inhibitors with respect to reducing the risk, signs or symptoms of Alport Syndrome.

In some embodiments, in addition to administration of aromatic-cationic peptides, the method also includes separately, sequentially or simultaneously administering to the subject one or more aldosterone inhibitors selected from the group consisting of spironolactone (Aldactone®), eplerenone (Inspra®), canrenone (canrenoate potassium), prorenone (prorenoate potassium), and mexrenone (mexrenoate potassium). In some embodiments of the methods of the present technology, there is a synergistic effect between the aromatic-cationic peptide and the aldosterone inhibitors with respect to reducing the risk, signs or symptoms of Alport Syndrome.

In some embodiments, in addition to administration of aromatic-cationic peptides, the method also includes separately, sequentially or simultaneously administering to the subject the matrix metalloproteinase inhibitor BAY-12-9566. In some embodiments of the methods of the present technology, there is a synergistic effect between the aromatic-cationic peptide and BAY-12-9566 with respect to reducing the risk, signs or symptoms of Alport Syndrome.

In one aspect, the present technology provides a method for treating a disease or condition characterized by a reduction of function, decreased expression level of, and/or deficiency in one or more of COL4A3, COL4A4 and COL4A5 genes in a subject in need thereof, comprising: administering to the subject a therapeutically effective amount of the aromatic-cationic peptide D-Arg-2',6'-Dmt-Lys-Phe-NH$_2$ or a pharmaceutically acceptable salt thereof. In some embodiments of the methods of the present technology, the pharmaceutically acceptable salt comprises acetate, tartrate, or trifluoroacetate salt.

In certain embodiments, the disease or condition is characterized by a reduction of function in one or more of COL4A3, COL4A4, and COL4A5 compared to a normal control subject. In other embodiments, the disease or condition is characterized by a deficiency in one or more of COL4A3, COL4A4, and COL4A5. In some embodiments of the methods of the present technology, the disease or condition is characterized by decreased expression levels of one or more of COL4A3, COL4A4, and COL4A5 compared to a normal control subject.

In some embodiments of the methods of the present technology, the subject has increased expression of MMP-9 in mesangial cells compared to a normal control subject. Additionally or alternatively, in some embodiments of the methods of the present technology, the subject has altered urine levels of one or more of ADAM8, fibronectin, myosin 10, MMP-2, and podocin compared to a normal control subject.

In some embodiments of the methods of the present technology, a combination of three urine biomarkers is altered in the subject compared to a normal control subject. In one particular embodiment, the subject has altered urine levels of fibronectin, myosin 10, and MMP-2 compared to a normal control subject. In another embodiment, the subject has altered urine levels of fibronectin, myosin 10, and MMP-9 compared to a normal control subject.

In other embodiments of the methods of the present technology, a combination of two urine biomarkers is altered in the subject compared to a normal control subject. In one particular embodiment, the subject has altered urine levels of myosin 10 and MMP-2 compared to a normal control subject. In another embodiment, the subject has altered urine levels of myosin 10 and MMP-9 compared to a normal control subject. In some embodiments of the methods of the present technology, the subject is human.

Additionally or alternatively, in some embodiments of the method, peptide treatment results in elevated Mfn1 expression and/or function compared to an untreated subject having the disease or condition characterized by a reduction of function, decreased expression level of, and/or deficiency in one or more of COL4A3, COL4A4 and COL4A5 genes.

In some embodiments of the methods of the present technology, the aromatic-cationic peptide is administered orally, topically, intranasally, systemically, intravenously, subcutaneously, intraperitoneally, intradermally, intraocularly, iontophoretically, transmucosally, or intramuscularly.

In some embodiments of the methods of the present technology, the aromatic-cationic peptide is administered daily for 1 week or more. In some embodiments of the methods of the present technology, the aromatic-cationic peptide is administered daily for 2 weeks or more. In some embodiments of the methods of the present technology, the aromatic-cationic peptide is administered daily for 3 weeks or more. In some embodiments of the methods of the present technology, the aromatic-cationic peptide is administered daily for 4 weeks or more. In some embodiments of the methods of the present technology, the aromatic-cationic peptide is administered daily for 6 weeks or more. In some embodiments of the methods of the present technology, the aromatic-cationic peptide is administered daily for 12 weeks or more.

Additionally or alternatively, in some embodiments, the methods of the present technology further comprise separately, sequentially or simultaneously administering one or more additional therapeutic agents to the subject. In a further embodiment, the combination of peptide and additional therapeutic agent has a synergistic effect in the prevention or treatment of the disease or condition characterized by a reduction of function, decreased expression level of, and/or deficiency in one or more of COL4A3, COL4A4 and COL4A5 genes.

In some embodiments of the methods, the additional therapeutic agents are selected from the group consisting of: angiotensin II converting enzyme inhibitors (ACE inhibitors), angiotensin II receptor blockers (ARBs), HMG-CoA reductase inhibitors, aldosterone inhibitors, aliskiren, calcineurin inhibitors (e.g., cyclosporine A, tacrolimus), endothelin receptor antagonists (e.g., sitaxentan, ambrisentan (LETAIRIS), atrasentan, BQ-123, zibotentan, bosentan (TRACLEER), macitentan, tezosentan, BQ-788 and A192621), sulodexide, vasopeptidase inhibitors (e.g., AVE7688), anti-transforming growth factor-β1 antibody, chemokine receptor 1 blockers, bone morphogenetic protein-7, PPARγ agonists (e.g., rosiglitazone, pioglitazone, MRL24, Fmoc-L-Leu, SR1664, SR1824, GW0072, MCC555, CLX-0921, PAT5A, L-764406, nTZDpa, CDDO (2-cyano-3,12-dioxooleana-1,9-dien-28-oic acid), ragaglitazar, O-arylmandelic acids, and NSAIDs) and BAY-12-9566.

In one aspect, the disclosure provides a method of treating or preventing Alport Syndrome in a mammalian subject, comprising administering to said mammalian subject a therapeutically effective amount of an aromatic-cationic peptide. In some embodiments, the aromatic-cationic peptide is a peptide having:

at least one net positive charge;
a minimum of four amino acids;
a maximum of about twenty amino acids;
a relationship between the minimum number of net positive charges ($p_m$) and the total number of amino acid residues (r) wherein $3p_m$ is the largest number that is less than or equal to r+1; and a relationship between the minimum number of aromatic groups (a) and the total number of net positive charges ($p_t$) wherein 2a is the largest number that is less than or equal to $p_t$+1, except that when a is 1, $p_t$ may also be 1. In particular embodiments, the mammalian subject is a human.

In one embodiment, $2p_m$ is the largest number that is less than or equal to r+1, and may be equal to $p_t$. The aromatic-cationic peptide may be a water-soluble peptide having a minimum of two or a minimum of three positive charges.

In one embodiment, the peptide comprises one or more non-naturally occurring amino acids, for example, one or more D-amino acids. In some embodiments, the C-terminal carboxyl group of the amino acid at the C-terminus is amidated. In certain embodiments, the peptide has a minimum of four amino acids. The peptide may have a total of about 6, a total of about 9, or a total of about 12 amino acids.

In one embodiment, the peptide may have the formula Phe-D-Arg-Phe-Lys-NH$_2$ or 2',6'-Dmp-D-Arg-Phe-Lys-NH$_2$. In a particular embodiment, the aromatic-cationic peptide has the formula D-Arg-2',6'-Dmt-Lys-Phe-NH$_2$.

In one embodiment, the peptide is defined by formula I:

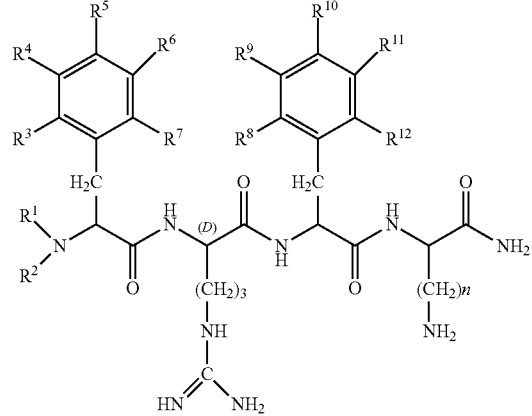

wherein $R^1$ and $R^2$ are each independently selected from
(i) hydrogen;
(ii) linear or branched $C_1$-$C_6$ alkyl;

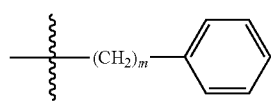

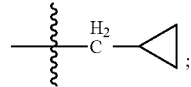

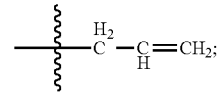

$R^3$, $R^4$, $R^5$, $R^6$, $R^7$, $R^8$, $R^9$, $R^{10}$, $R^{11}$ and $R^{12}$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo; and n is an integer from 1 to 5.

In a particular embodiment, $R^1$, $R^2$, $R^3$, $R^4$, $R^5$, $R^6$, $R^7$, $R^8$, $R^9$, $R^{10}$, $R^{11}$ and $R^{12}$ are all hydrogen; and n is 4. In another embodiment, $R^1$, $R^2$, $R^3$, $R^4$, $R^5$, $R^6$, $R^7$, $R^8$, $R^9$, and $R^{11}$ are all hydrogen; $R^8$ and $R^{12}$ are methyl; $R^{10}$ is hydroxyl; and n is 4.

In one embodiment, the peptide is defined by formula II:

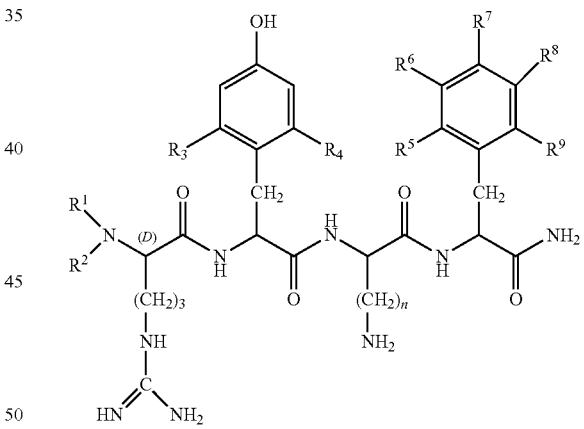

wherein $R^1$ and $R^2$ are each independently selected from
(i) hydrogen;
(ii) linear or branched $C_1$-$C_6$ alkyl;

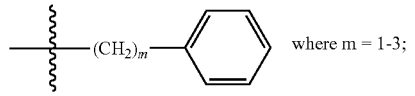

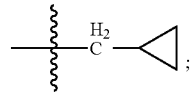

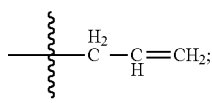

(v)

R³ and R⁴ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo; R⁵, R⁶, R⁷, R⁸, and R⁹ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo; and n is an integer from 1 to 5.

In a particular embodiment, R1 and R2 are hydrogen; R3 and R4 are methyl; R5, R6, R7, R8, and R9 are all hydrogen; and n is 4.

In some embodiments, the aromatic-cationic peptides of the present technology have a core structural motif of alternating aromatic and cationic amino acids. For example, the peptide may be a tetrapeptide defined by any of Formulas A to F set forth below:

| | |
|---|---|
| Aromatic-Cationic-Aromatic-Cationic | (Formula A) |
| Cationic-Aromatic-Cationic-Aromatic | (Formula B) |
| Aromatic-Aromatic-Cationic-Cationic | (Formula C) |
| Cationic-Cationic-Aromatic-Aromatic | (Formula D) |
| Aromatic-Cationic-Cationic-Aromatic | (Formula E) |
| Cationic-Aromatic-Aromatic-Cationic | (Formula F) | wherein, Aromatic is a residue selected from the group consisting of: Phe (F), Tyr (Y), and Trp (W). In some embodiments, the Aromatic residue may be substituted with a saturated analog of an aromatic residue, e.g., Cyclohexylalanine (Cha). In some embodiments, Cationic is a residue selected from the group consisting of: Arg (R), Lys (K), and His (H).

BRIEF DESCRIPTION OF THE DRAWINGS

FIG. 1 shows the 5 stages of Alport nephropathy, adapted from Kashtan et al., *Pediatr. Nephrol.* 28: 5-11 (2013).

DETAILED DESCRIPTION

Figure 2:
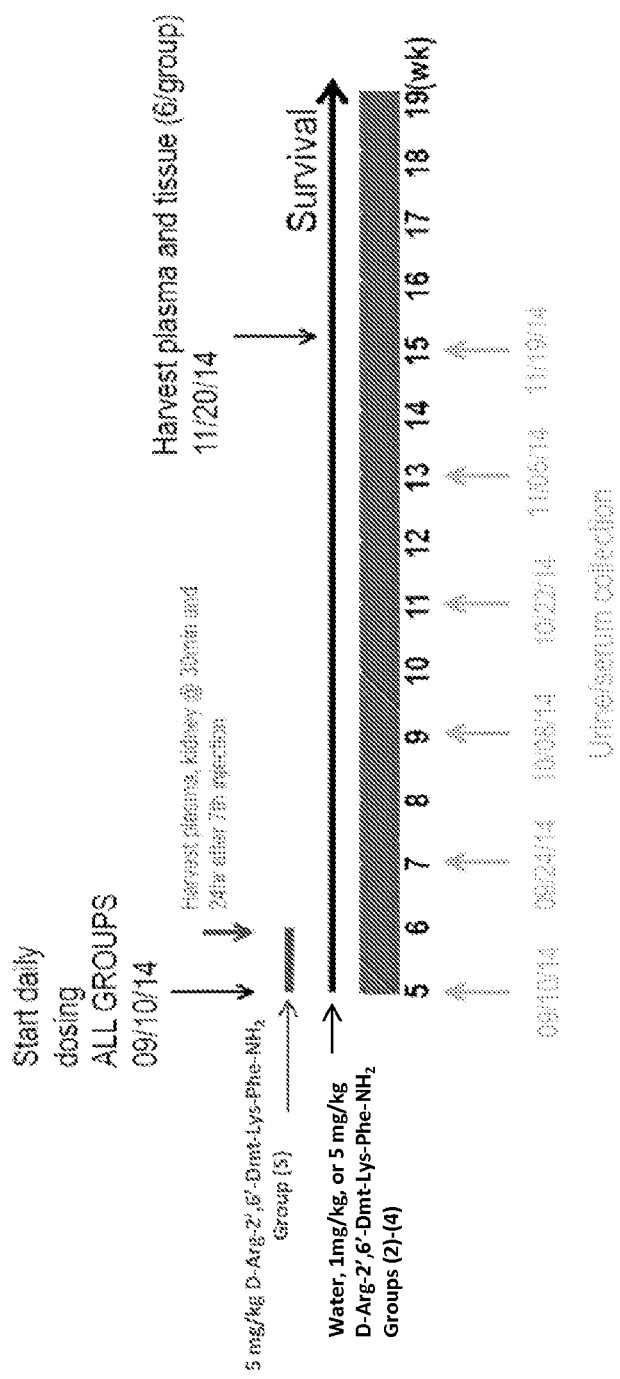
FIG. 2 shows the overall study design for evaluating of D-Arg-2',6'-Dmt-Lys-Phe-NH₂ administration on renal dysfunction in a Col4a3 null mouse model.

It is to be appreciated that certain aspects, modes, embodiments, variations and features of the present technology are described below in various levels of detail in order to provide a substantial understanding of the present technology. The definitions of certain terms as used in this specification are provided below. Unless defined otherwise, all technical and scientific terms used herein generally have the same meaning as commonly understood by one of ordinary skill in the art to which this present technology belongs.

As used in this specification and the appended claims, the singular forms "a", "an" and "the" include plural referents unless the content clearly dictates otherwise. For example, reference to "a cell" includes a combination of two or more cells, and the like.

As used herein, the "administration" of an agent, drug, or peptide to a subject includes any route of introducing or delivering to a subject a compound to perform its intended function. Administration can be carried out by any suitable route, including orally, intranasally, parenterally (intravenously, intramuscularly, intraperitoneally, or subcutaneously), systemically, intradermally, intraocularly, iontophoretically, transmucosally, intramuscularly, or topically. Administration includes self-administration and the administration by another.

As used herein, the term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid Amino acids can be referred to herein by either their commonly known three letter symbols or by the one-letter symbols recommended by the IUPAC-IUB Biochemical Nomenclature Commission.

As used herein, the term "effective amount" refers to a quantity sufficient to achieve a desired therapeutic and/or prophylactic effect, e.g., an amount which results in the full or partial restoration of the structural integrity and function of basement membranes in the kidney, inner ear, and eye in a subject in need thereof, or which results in partial or full amelioration of one or more symptoms of Alport Syndrome. In the context of therapeutic or prophylactic applications, in some embodiments, the amount of a composition administered to the subject will depend on the type, degree, and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, aromatic-cationic peptides, such as D-Arg-2',6'-Dmt-Lys-Phe-NH$_2$, or a pharmaceutically acceptable salt thereof, such as acetate, tartrate, or trifluoroacetate salt, may be administered to a subject having one or more signs, symptoms, or risk factors of Alport Syndrome, including, but not limited to, hematuria, proteinuria, cylindruria, leukocyturia, hypertension, edema, microalbuminuria, declining glomerular filtration rate, interstitial fibrosis, interstitial inflammation, tubular damage, GBM ultrastructural abnormalities, nephrotic syndrome, glomerulonephritis, end-stage kidney disease, chronic anemia, macrothrombocytopenia, osteodystrophy, sensorineural deafness, anterior lenticonus, dot-and-fleck retinopathy, posterior polymorphous corneal dystrophy, recurrent corneal erosion, temporal macular thinning, cataracts, lacrimation, photophobia, vision loss, keratoconus, and leiomyomatosis. For example, a "therapeutically effective amount" of the aromatic-cationic peptides includes levels at which the presence, frequency, or severity of one or more signs, symptoms, or risk factors of Alport Syndrome are reduced or eliminated. In some embodiments, a therapeutically effective amount reduces or ameliorates the physiological effects of Alport Syndrome, and/or the risk factors of Alport Syndrome, and/or the likelihood of developing Alport Syndrome.

As used herein, "isolated" or "purified" polypeptide or peptide refers to a polypeptide or peptide that is substantially free of cellular material or other contaminating polypeptides from the cell or tissue source from which the agent is derived, or substantially free from chemical precursors or other chemicals when chemically synthesized. For example, an isolated aromatic-cationic peptide would be free of materials that would interfere with diagnostic or therapeutic uses of the agent. Such interfering materials may include enzymes, hormones and other proteinaceous and nonproteinaceous solutes.

As used herein, the terms "polypeptide," "peptide," and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art.

As used herein, the terms "subject," "individual," or "patient" can be an individual organism, a vertebrate, a mammal, or a human.

As used herein, the term "simultaneous" therapeutic use refers to the administration of at least two active ingredients by the same route and at the same time or at substantially the same time.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

A "synergistic therapeutic effect" refers to a greater-than-additive therapeutic effect which is produced by a combination of at least two therapeutic agents, and which exceeds that which would otherwise result from the individual administration of the agents. For example, lower doses of one or more therapeutic agents may be used in treating Alport Syndrome, resulting in increased therapeutic efficacy and decreased side-effects.

As used herein, the terms "treating" or "treatment" or "alleviation" refers to therapeutic treatment, wherein the object is to reduce, alleviate or slow down the progression or advancement of, and/or reverse the progression of the targeted pathological condition or disorder. A subject is successfully "treated" for Alport Syndrome if, after receiving a therapeutic amount of the aromatic-cationic peptides, such as D-Arg-2',6'-Dmt-Lys-Phe-NH$_2$, or a pharmaceutically acceptable salt thereof, such as acetate, tartrate, or trifluoroacetate salt, according to the methods described herein, the subject shows observable and/or measurable reduction in or absence of one or more signs and symptoms of Alport Syndrome, such as, e.g., but not limited to, hematuria, proteinuria, cylindruria, leukocyturia, hypertension, edema, microalbuminuria, declining glomerular filtration rate, interstitial fibrosis, interstitial inflammation, tubular damage, GBM ultrastructural abnormalities, nephrotic syndrome, glomerulonephritis, end-stage kidney disease, chronic anemia, macrothrombocytopenia, osteodystrophy, sensorineural deafness, anterior lenticonus, dot-and-fleck retinopathy, posterior polymorphous corneal dystrophy, recurrent corneal erosion, temporal macular thinning, cataracts, lacrimation, photophobia, vision loss, keratoconus, and leiomyomatosis.

As used herein, "prevention" or "preventing" of a disorder or condition refers to a compound that, in a statistical sample, reduces the occurrence of the disorder or condition in the treated sample relative to an untreated control sample, or delays the onset of one or more symptoms of the disorder or condition relative to the untreated control sample. As used herein, preventing Alport Syndrome includes preventing or delaying the initiation of Alport Syndrome. As used herein, prevention of Alport Syndrome also includes preventing a recurrence of one or more signs or symptoms of Alport Syndrome.

It is also to be appreciated that the various modes of treatment or prevention of medical conditions as described herein are intended to mean "substantial," which includes total but also less than total treatment or prevention, and wherein some biologically or medically relevant result is achieved.

Aromatic-Cationic Peptides

The present technology relates to methods and compositions for preventing or treating Alport Syndrome in a subject in need thereof, and/or for preventing, ameliorating, or reducing the severity of one or more signs, or symptoms associated with a reduction of function, decreased expression level of, and/or a deficiency in genes that are components of the Type IV collagen alpha3-4-5 network. It is expected that administration of aromatic-cationic peptides will not only be effective for the treatment or prevention of Alport Syndrome and/or preventing, ameliorating, or reducing the severity of one or more signs, or symptoms associated with a reduction of function, decreased expression level of, and/or a deficiency in genes that are components of the Type IV collagen alpha3-4-5 network, but that administration of the peptides in combination with additional therapeutic agents will have synergistic effects in treatment or prevention of the disease. For example, administration of the peptides in combination with conventional or newly developed agents for the treatment of Alport Syndrome will have greater than additive effects in the prevention or treatment of the disease.

In some embodiments, the methods and compositions prevent one or more signs or symptoms of Alport Syndrome in a subject, and/or prevent, ameliorate, or reduce the severity of one or more signs, or symptoms associated with a reduction of function, decreased expression level of, and/or a deficiency in genes that are components of the Type IV collagen alpha3-4-5 network. In some embodiments, the methods and compositions reduce the likelihood that a subject with risk factors for Alport Syndrome will develop one or more signs or symptoms of Alport Syndrome. Exemplary risk factors include, but are not limited to mutations in COL4A3, COL4A4, and COL4A5.

In one embodiment, the peptide is defined by formula I:

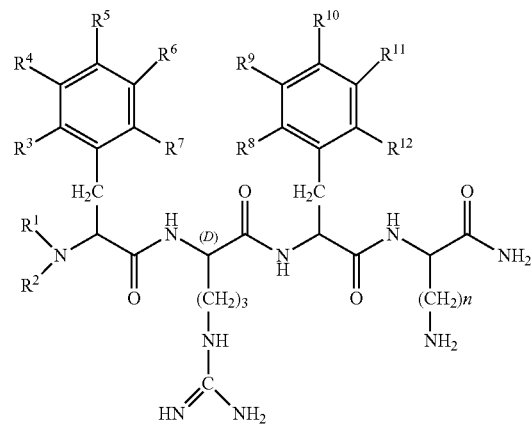

wherein $R^1$ and $R^2$ are each independently selected from
(i) hydrogen;
(ii) linear or branched $C_1$-$C_6$ alkyl;

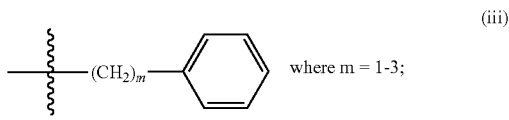

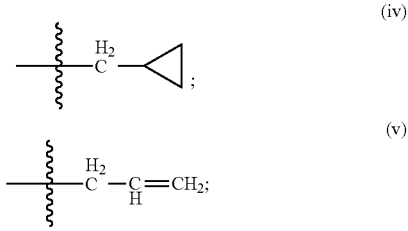

$R^3$, $R^4$, $R^5$, $R^6$, $R^7$, $R^8$, $R^9$, $R^{10}$, $R^{11}$ and $R^{12}$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo; and n is an integer from 1 to 5.

In a particular embodiment, $R^1$, $R^2$, $R^3$, $R^4$, $R^5$, $R^6$, $R^7$, $R^8$, $R^9$, $R^{10}$, $R^{11}$ and $R^{12}$ are all hydrogen; and n is 4. In another embodiment, $R^1$, $R^2$, $R^3$, $R^4$, $R^5$, $R^6$, $R^7$, $R^8$, $R^9$, and $R^{11}$ are all hydrogen; $R^8$ and $R^{12}$ are methyl; $R^{10}$ is hydroxyl; and n is 4.

In one embodiment, the peptide is defined by formula II:

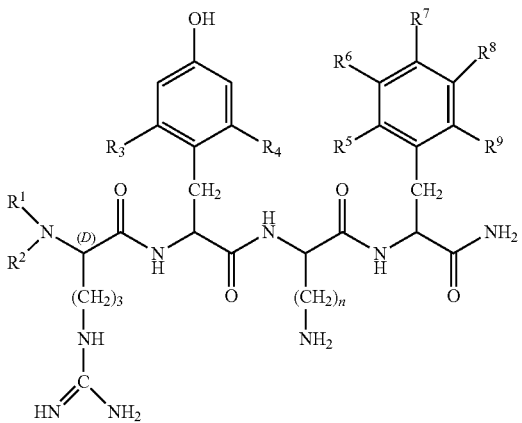

wherein $R^1$ and $R^2$ are each independently selected from
(i) hydrogen;
(ii) linear or branched $C_1$-$C_6$ alkyl;

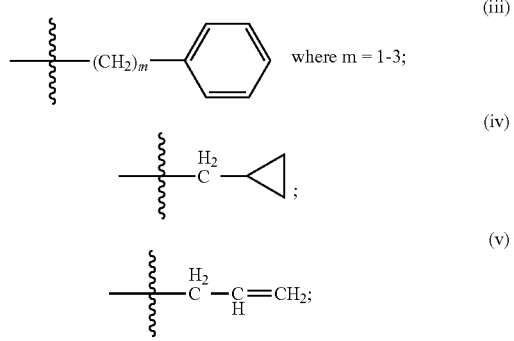

$R^3$ and $R^4$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo;
$R^5$, $R^6$, $R^7$, $R^8$, and $R^9$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ di alkyl amino;
(vii) nitro;
(viii) hydroxyl;
(ix) halogen, where "halogen" encompasses chloro, fluoro, bromo, and iodo; and n is an integer from 1 to 5.

In a particular embodiment, $R^1$ and $R^2$ are hydrogen; $R^3$ and $R^4$ are methyl; $R^5$, $R^6$, $R^7$, $R^8$, and $R^9$ are all hydrogen; and n is 4.

In some embodiments, the aromatic-cationic peptides of the present technology have a core structural motif of alternating aromatic and cationic amino acids. For example, the peptide may be a tetrapeptide defined by any of Formulas A to F set forth below:

| | |
|---|---|
| Aromatic-Cationic-Aromatic-Cationic | (Formula A) |
| Cationic-Aromatic-Cationic-Aromatic | (Formula B) |
| Aromatic-Aromatic-Cationic-Cationic | (Formula C) |
| Cationic-Cationic-Aromatic-Aromatic | (Formula D) |
| Aromatic-Cationic-Cationic-Aromatic | (Formula E) |
| Cationic-Aromatic-Aromatic-Cationic | (Formula F) | wherein, Aromatic is a residue selected from the group consisting of: Phe (F), Tyr (Y), and Trp (W). In some embodiments, the Aromatic residue may be substituted with a saturated analog of an aromatic residue, e.g., Cyclohexylalanine (Cha). In some embodiments, Cationic is a residue selected from the group consisting of: Arg (R), Lys (K), and His (H).

The aromatic-cationic peptides are water-soluble and highly polar. Despite these properties, the peptides can readily penetrate cell membranes. The aromatic-cationic peptides typically include a minimum of three amino acids or a minimum of four amino acids, covalently joined by peptide bonds. The maximum number of amino acids present in the aromatic-cationic peptides is about twenty amino acids covalently joined by peptide bonds. In some embodiments, the total number of amino acids is about twelve, about nine, or about six.

The amino acids of the aromatic-cationic peptides can be any amino acid. As used herein, the term "amino acid" is used to refer to any organic molecule that contains at least one amino group and at least one carboxyl group. Typically, at least one amino group is at the α position relative to a carboxyl group. The amino acids may be naturally occurring. Naturally occurring amino acids include, for example, the twenty most common levorotatory (L) amino acids normally found in mammalian proteins, i.e., alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan, (Trp), tyrosine (Tyr), and valine (Val). Other naturally occurring amino acids include, for example, amino acids that are synthesized in metabolic processes not associated with protein synthesis. For example, the amino acids ornithine and citrulline are synthesized in mammalian metabolism during the production of urea. Another example of a naturally occurring amino acid includes hydroxyproline (Hyp).

The peptides optionally contain one or more non-naturally occurring amino acids. Optimally, the peptide has no amino acids that are naturally occurring. The non-naturally occurring amino acids may be levorotary (L-), dextrorotatory (D-), or mixtures thereof. Non-naturally occurring amino acids are those amino acids that typically are not synthesized in normal metabolic processes in living organisms, and do not naturally occur in proteins. In addition, the non-naturally occurring amino acids suitably are also not recognized by common proteases. The non-naturally occurring amino acid can be present at any position in the peptide. For example, the non-naturally occurring amino acid can be at the N-terminus, the C-terminus, or at any position between the N-terminus and the C-terminus.

The non-natural amino acids may, for example, comprise alkyl, aryl, or alkylaryl groups not found in natural amino acids. Some examples of non-natural alkyl amino acids include α-aminobutyric acid, β-aminobutyric acid, γ-aminobutyric acid, δ-aminovaleric acid, and ε-aminocaproic acid. Some examples of non-natural aryl amino acids include ortho-, meta-, and para-aminobenzoic acid. Some examples of non-natural alkylaryl amino acids include ortho-, meta-, and para-aminophenylacetic acid, and γ-phenyl-β-aminobutyric acid. Non-naturally occurring amino acids include derivatives of naturally occurring amino acids. The derivatives of naturally occurring amino acids may, for example, include the addition of one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include branched or unbranched $C_1$-$C_4$ alkyl, such as methyl, ethyl, n-propyl, isopropyl, butyl, isobutyl, or t-butyl, $C_1$-$C_4$ alkyloxy (i.e., alkoxy), amino, $C_1$-$C_4$ alkylamino and $C_1$-$C_4$ dialkylamino (e.g., methylamino, dimethylamino), nitro, hydroxyl, halo (i.e., fluoro, chloro, bromo, or iodo). Some specific examples of non-naturally occurring derivatives of naturally occurring amino acids include norvaline (Nva) and norleucine (Nle).

Another example of a modification of an amino acid in a peptide is the derivatization of a carboxyl group of an aspartic acid or a glutamic acid residue of the peptide. One example of derivatization is amidation with ammonia or with a primary or secondary amine, e.g. methylamine, ethylamine, dimethylamine or diethylamine. Another example of derivatization includes esterification with, for example, methyl or ethyl alcohol. Another such modification includes derivatization of an amino group of a lysine, arginine, or histidine residue. For example, such amino groups can be acylated. Some suitable acyl groups include, for example, a benzoyl group or an alkanoyl group comprising any of the $C_1$-$C_4$ alkyl groups mentioned above, such as an acetyl or propionyl group.

The non-naturally occurring amino acids are suitably resistant or insensitive to common proteases. Examples of non-naturally occurring amino acids that are resistant or insensitive to proteases include the dextrorotatory (D-) form of any of the above-mentioned naturally occurring L-amino acids, as well as L- and/or D-non-naturally occurring amino acids. The D-amino acids do not normally occur in proteins, although they are found in certain peptide antibiotics that are synthesized by means other than the normal ribosomal protein synthetic machinery of the cell. As used herein, the D-amino acids are considered to be non-naturally occurring amino acids.

In order to minimize protease sensitivity, the peptides should have less than five, less than four, less than three, or less than two contiguous L-amino acids recognized by common proteases, irrespective of whether the amino acids are naturally or non-naturally occurring. Optimally, the peptide has only D-amino acids, and no L-amino acids. If the peptide contains protease sensitive sequences of amino acids, at least one of the amino acids may be a non-naturally-occurring D-amino acid, thereby conferring protease resistance. An example of a protease sensitive sequence includes two or more contiguous basic amino acids that are readily cleaved by common proteases, such as endopeptidases and trypsin. Examples of basic amino acids include arginine, lysine and histidine.

The aromatic-cationic peptides should have a minimum number of net positive charges at physiological pH in comparison to the total number of amino acid residues in the peptide. The minimum number of net positive charges at physiological pH will be referred to below as ($p_m$). The total number of amino acid residues in the peptide will be referred to below as (r). The minimum number of net positive charges discussed below are all at physiological pH. The term "physiological pH" as used herein refers to the normal pH in the cells of the tissues and organs of the mammalian body. For instance, the physiological pH of a human is normally approximately 7.4, but normal physiological pH in mammals may be any pH from about 7.0 to about 7.8.

"Net charge" as used herein refers to the balance of the number of positive charges and the number of negative charges carried by the amino acids present in the peptide. In this specification, it is understood that net charges are measured at physiological pH. The naturally occurring amino acids that are positively charged at physiological pH include L-lysine, L-arginine, and L-histidine. The naturally occurring amino acids that are negatively charged at physiological pH include L-aspartic acid and L-glutamic acid.

Typically, a peptide has a positively charged N-terminal amino group and a negatively charged C-terminal carboxyl group. The charges cancel each other out at physiological pH. As an example of calculating net charge, the peptide Tyr-Arg-Phe-Lys-Glu-His-Trp-D-Arg has one negatively charged amino acid (i.e., Glu) and four positively charged amino acids (i.e., two Arg residues, one Lys, and one His). Therefore, the above peptide has a net positive charge of three.

In one embodiment, the aromatic-cationic peptides have a relationship between the minimum number of net positive charges at physiological pH ($p_m$) and the total number of amino acid residues (r) wherein $3p_m$ is the largest number that is less than or equal to r+1. In this embodiment, the relationship between the minimum number of net positive charges ($p_m$) and the total number of amino acid residues (r) is as follows:

TABLE 2

| Amino acid number and net positive charges ($3p_m \leq p + 1$) | | | | | | | | | | | | | | | | | | |
|---|---|---|---|---|---|---|---|---|---|---|---|---|---|---|---|---|---|---|
| (r) | 3 | 4 | 5 | 6 | 7 | 8 | 9 | 10 | 11 | 12 | 13 | 14 | 15 | 16 | 17 | 18 | 19 | 20 |
| ($p_m$) | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of net positive charges ($p_m$) and the total number of amino acid residues (r) wherein $2p_m$ is the largest number that is less than or equal to r+1. In this embodiment, the relationship between the minimum number of net positive charges ($p_m$) and the total number of amino acid residues (r) is as follows:

TABLE 3

Amino acid number and net positive charges ($2p_m \leq p + 1$)

| (r) | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|
| ($p_m$) | 2 | 2 | 3 | 3 | 4 | 4 | 5 | 5 | 6 | 6 | 7 | 7 | 8 | 8 | 9 | 9 | 10 | 10 |

In one embodiment, the minimum number of net positive charges ($p_m$) and the total number of amino acid residues (r) are equal. In another embodiment, the peptides have three or four amino acid residues and a minimum of one net positive charge, suitably, a minimum of two net positive charges or three net positive charges.

It is also important that the aromatic-cationic peptides have a minimum number of aromatic groups in comparison to the total number of net positive charges ($p_t$). The minimum number of aromatic groups will be referred to below as (a). Naturally occurring amino acids that have an aromatic group include the amino acids histidine, tryptophan, tyrosine, and phenylalanine. For example, the hexapeptide Lys-Gln-Tyr-D-Arg-Phe-Trp has a net positive charge of two (contributed by the lysine and arginine residues) and three aromatic groups (contributed by tyrosine, phenylalanine and tryptophan residues).

The aromatic-cationic peptides should also have a relationship between the minimum number of aromatic groups (a) and the total number of net positive charges at physiological pH ($p_t$) wherein 3a is the largest number that is less than or equal to $p_t+1$, except that when $p_t$ is 1, a may also be 1. In this embodiment, the relationship between the minimum number of aromatic groups (a) and the total number of net positive charges ($p_t$) is as follows:

TABLE 4

Aromatic groups and net positive charges ($3a \leq p_t + 1$ or $a = p_t = 1$)

| ($p_t$) | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| (a) | 1 | 1 | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of aromatic groups (a) and the total number of net positive charges ($p_t$) wherein 2a is the largest number that is less than or equal to $p_t+1$. In this embodiment, the relationship between the minimum number of aromatic amino acid residues (a) and the total number of net positive charges ($p_t$) is as follows:

TABLE 5

Aromatic groups and net positive charges ($2a \leq p_t + 1$ or $a = p_t = 1$)

| ($p_t$) | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| (a) | 1 | 1 | 2 | 2 | 3 | 3 | 4 | 4 | 5 | 5 | 6 | 6 | 7 | 7 | 8 | 8 | 9 | 9 | 10 | 10 |

In another embodiment, the number of aromatic groups (a) and the total number of net positive charges ($p_t$) are equal.

Carboxyl groups, especially the terminal carboxyl group of a C-terminal amino acid, are suitably amidated with, for example, ammonia to form the C-terminal amide. Alternatively, the terminal carboxyl group of the C-terminal amino acid may be amidated with any primary or secondary amine. The primary or secondary amine may, for example, be an alkyl, especially a branched or unbranched $C_1$-$C_4$ alkyl, or an aryl amine. Accordingly, the amino acid at the C-terminus of the peptide may be converted to an amido, N-methylamido, N-ethylamido, N,N-dimethylamido, N,N-diethylamido, N-methyl-N-ethylamido, N-phenylamido or N-phenyl-N-ethylamido group. The free carboxylate groups of the asparagine, glutamine, aspartic acid, and glutamic acid residues not occurring at the C-terminus of the aromatic-cationic peptides may also be amidated wherever they occur within the peptide. The amidation at these internal positions may be with ammonia or any of the primary or secondary amines described above.

In one embodiment, the aromatic-cationic peptide is a tripeptide having two net positive charges and at least one aromatic amino acid. In a particular embodiment, the aromatic-cationic peptide is a tripeptide having two net positive charges and two aromatic amino acids.

Aromatic-cationic peptides include, but are not limited to, the following peptide examples:

TABLE 6

EXEMPLARY PEPTIDES

2',6'-Dmp-D-Arg-2',6'-Dmt-Lys-NH₂
2',6'-Dmp-D-Arg-Phe-Lys-NH₂
2',6'-Dmt-D-Arg-PheOrn-NH₂
2',6'-Dmt-D-Arg-Phe-Ahp(2-aminoheptanoicacid)-NH₂
2',6'-Dmt-D-Arg-Phe-Lys-NH₂
2',6'-Dmt-D-Cit-PheLys-NH₂
Ala-D-Phe-D-Arg-Tyr-Lys-D-Trp-His-D-Tyr-Gly-Phe
Arg-D-Leu-D-Tyr-Phe-Lys-Glu-D-Lys-Arg-D-Trp-Lys-D-Phe-Tyr-D-Arg-Gly
Asp-Arg-D-Phe-Cys-Phe-D-Arg-D-Lys-Tyr-Arg-D-Tyr-Trp-D-His-Tyr-D-Phe-Lys-Phe
Asp-D-Trp-Lys-Tyr-D-His-Phe-Arg-D-Gly-Lys-NH₂
D-Arg-2',6'-Dmt-Lys-Phe-NH₂
D-Glu-Asp-Lys-D-Arg-D-His-Phe-Phe-D-Val-Tyr-Arg-Tyr-D-Tyr-Arg-His-Phe-NH₂
D-His-Glu-Lys-Tyr-D-Phe-Arg
D-His-Lys-Tyr-D-Phe-Glu-D-Asp-D-Asp-D-His-D-Lys-Arg-Trp-NH₂
D-Tyr-Trp-Lys-NH₂
Glu-Arg-D-Lys-Tyr-D-Val-Phe-D-His-Trp-Arg-D-Gly-Tyr-Arg-D-Met-NH₂
Gly-Ala-Lys-Phe-D-Lys-Glu-Arg-Tyr-His-D-Arg-D-Arg-Asp-Tyr-Trp-D-His-Trp-His-D-Lys-Asp.
Gly-D-Phe-Lys-His-D-Arg-Tyr-NH₂
His-Tyr-D-Arg-Trp-Lys-Phe-D-Asp-Ala-Arg-Cys-D-Tyr-His-Phe-D-Lys-Tyr-His-Ser-NH₂
Lys-D-Arg-Tyr-NH₂
Lys-D-Gln-Tyr-Arg-D-Phe-Trp-NH₂
Lys-Trp-D-Tyr-Arg-Asn-Phe-Tyr-D-His-NH₂
Met-Tyr-D-Arg-Phe-Arg-NH₂
Met-Tyr-D-Lys-Phe-Arg
Phe-Arg-D-His-Asp
Phe-D-Arg-2',6'-Dmt-Lys-NH₂
Phe-D-Arg-His
Phe-D-Arg-Lys-Trp-Tyr-D-Arg-His
Phe-D-Arg-Phe-Lys-NH₂
Phe-Phe-D-Tyr-Arg-Glu-Asp-D-Lys-Arg-D-Arg-His-Phe-NH₂
Phe-Tyr-Lys-D-Arg-Trp-His-D-Lys-D-Lys-Glu-Arg-D-Tyr-Thr
Thr-Gly-Tyr-Arg-D-His-Phe-Trp-D-His-Lys
Thr-Tyr-Arg-D-Lys-Trp-Tyr-Glu-Asp-D-Lys-D-Arg-His-Phe-D-Tyr-Gly-Val-Ile-D-His-Arg-Tyr-Lys-NH₂
Trp-D-Lys-Tyr-Arg-NH₂
Trp-Lys-Phe-D-Asp-Arg-Tyr-D-His-Lys
Tyr-Asp-D-Lys-Tyr-Phe-D-Lys-D-Arg-Phe-Pro-D-Tyr-His-Lys
Tyr-D-Arg-Phe-Lys-Glu-NH₂
Tyr-D-Arg-Phe-Lys-NH₂
Tyr-D-His-Phe-D-Arg-Asp-Lys-D-Arg-His-Trp-D-His-Phe
Tyr-His-D-Gly-Met
Val-D-Lys-His-Tyr-D-Phe-Ser-Tyr-Arg-NH₂

In one embodiment, the peptides have mu-opioid receptor agonist activity (i.e., they activate the mu-opioid receptor). Peptides, which have mu-opioid receptor agonist activity, are typically those peptides that have a tyrosine residue or a tyrosine derivative at the N-terminus (i.e., the first amino acid position). Suitable derivatives of tyrosine include 2'-methyltyrosine (Mmt); 2',6'-dimethyltyrosine (2',6'-Dmt); 3',5'-dimethyltyrosine (3',5'-Dmt); N,2',6'-trimethyltyrosine (Tmt); and 2'-hydroxy-6'-methyltryosine (Hmt).

In one embodiment, a peptide that has mu-opioid receptor agonist activity has the formula Tyr-D-Arg-Phe-Lys-NH₂. Tyr-D-Arg-Phe-Lys-NH₂ has a net positive charge of three, contributed by the amino acids tyrosine, arginine, and lysine and has two aromatic groups contributed by the amino acids phenylalanine and tyrosine. The tyrosine of Tyr-D-Arg-Phe-Lys-NH₂ can be a modified derivative of tyrosine such as in 2',6'-dimethyltyrosine to produce the compound having the formula 2',6'-Dmt-D-Arg-Phe-Lys-NH₂. 2',6'-Dmt-D-Arg-Phe-Lys-NH₂ has a molecular weight of 640 and carries a net three positive charge at physiological pH. 2',6'-Dmt-D-Arg-Phe-Lys-NH₂ readily penetrates the plasma membrane of several mammalian cell types in an energy-independent manner (Zhao, et al., *J. Pharmacol Exp Ther.*, 304:425-432, 2003).

Alternatively, in other instances, the aromatic-cationic peptide does not have mu-opioid receptor agonist activity. For example, during long-term treatment, such as in a chronic disease state or condition, the use of an aromatic-cationic peptide that activates the mu-opioid receptor may be contraindicated. In these instances, the potentially adverse or addictive effects of the aromatic-cationic peptide may preclude the use of an aromatic-cationic peptide that activates the mu-opioid receptor in the treatment regimen of a human patient or other mammal. Potential adverse effects may include sedation, constipation and respiratory depression. In such instances an aromatic-cationic peptide that does not activate the mu-opioid receptor may be an appropriate treatment. Peptides that do not have mu-opioid receptor agonist activity generally do not have a tyrosine residue or a derivative of tyrosine at the N-terminus (i.e., amino acid position 1). The amino acid at the N-terminus can be any naturally occurring or non-naturally occurring amino acid other than tyrosine. In one embodiment, the amino acid at the N-terminus is phenylalanine or its derivative. Exemplary derivatives of phenylalanine include 2'-methylphenylalanine (Mmp), 2',6'-dimethylphenylalanine (2',6'-Dmp), N,2',6'-trimethylphenylalanine (Tmp), and 2'-hydroxy-6'-methylphenylalanine (Hmp).

An example of an aromatic-cationic peptide that does not have mu-opioid receptor agonist activity has the formula Phe-D-Arg-Phe-Lys-NH₂. Alternatively, the N-terminal phenylalanine can be a derivative of phenylalanine such as 2',6'-dimethylphenylalanine (2'6'-Dmp). Tyr-D-Arg-Phe-Lys-NH₂ containing 2',6'-dimethylphenylalanine at amino acid position 1 has the formula 2',6'-Dmp-D-Arg-Phe-Lys-NH₂. In one embodiment, the amino acid sequence of 2',6'-Dmt-D-Arg-Phe-Lys-NH₂ is rearranged such that Dmt is not at the N-terminus. An example of such an aromatic-cationic peptide that does not have mu-opioid receptor agonist activity has the formula D-Arg-2',6'-Dmt-Lys-Phe-NH₂.

Suitable substitution variants of the peptides listed herein include conservative amino acid substitutions. Amino acids may be grouped according to their physicochemical characteristics as follows:

(a) Non-polar amino acids: Ala(A) Ser(S) Thr(T) Pro(P) Gly(G) Cys (C);
(b) Acidic amino acids: Asn(N) Asp(D) Glu(E) Gln(Q);
(c) Basic amino acids: His(H) Arg(R) Lys(K);
(d) Hydrophobic amino acids: Met(M) Leu(L) Ile(I) Val (V); and
(e) Aromatic amino acids: Phe(F) Tyr(Y) Trp(W) His (H).

Substitutions of an amino acid in a peptide by another amino acid in the same group is referred to as a conservative substitution and may preserve the physicochemical characteristics of the original peptide. In contrast, substitutions of an amino acid in a peptide by another amino acid in a different group are generally more likely to alter the characteristics of the original peptide.

Examples of peptides that activate mu-opioid receptors include, but are not limited to, the aromatic-cationic peptides shown in Table 7.

TABLE 7

Peptide Analogs with Mu-Opioid Activity

| Amino Acid Position 1 | Amino Acid Position 2 | Amino Acid Position 3 | Amino Acid Position 4 | C-Terminal Modification |
| --- | --- | --- | --- | --- |
| Tyr | D-Arg | Phe | Lys | NH₂ |
| Tyr | D-Arg | Phe | Orn | NH₂ |
| Tyr | D-Arg | Phe | Dab | NH₂ |
| Tyr | D-Arg | Phe | Dap | NH₂ |
| 2',6'-Dmt | D-Arg | Phe | Lys | NH₂ |
| 2',6'-Dmt | D-Arg | Phe | Lys-NH(CH₂)₂—NH-dns | NH₂ |
| 2',6'-Dmt | D-Arg | Phe | Lys-NH(CH₂)₂—NH-atn | NH₂ |
| 2',6'-Dmt | D-Arg | Phe | dnsLys | NH₂ |
| 2',6'-Dmt | D-Cit | Phe | Lys | NH₂ |
| 2',6'-Dmt | D-Cit | Phe | Ahp | NH₂ |
| 2',6'-Dmt | D-Arg | Phe | Orn | NH₂ |
| 2',6'-Dmt | D-Arg | Phe | Dab | NH₂ |
| 2',6'-Dmt | D-Arg | Phe | Dap | NH₂ |
| 2',6'-Dmt | D-Arg | Phe | Ahp(2-aminoheptanoic acid) | NH₂ |
| Bio-2',6'-Dmt | D-Arg | Phe | Lys | NH₂ |
| 3',5'-Dmt | D-Arg | Phe | Lys | NH₂ |
| 3',5'-Dmt | D-Arg | Phe | Orn | NH₂ |
| 3',5'-Dmt | D-Arg | Phe | Dab | NH₂ |
| 3',5'-Dmt | D-Arg | Phe | Dap | NH₂ |
| Tyr | D-Arg | Tyr | Lys | NH₂ |
| Tyr | D-Arg | Tyr | Orn | NH₂ |
| Tyr | D-Arg | Tyr | Dab | NH₂ |
| Tyr | D-Arg | Tyr | Dap | NH₂ |
| 2',6'-Dmt | D-Arg | Tyr | Lys | NH₂ |
| 2',6'-Dmt | D-Arg | Tyr | Orn | NH₂ |
| 2',6'-Dmt | D-Arg | Tyr | Dab | NH₂ |
| 2',6'-Dmt | D-Arg | Tyr | Dap | NH₂ |
| 2',6'-Dmt | D-Arg | 2',6'-Dmt | Lys | NH₂ |
| 2',6'-Dmt | D-Arg | 2',6'-Dmt | Orn | NH₂ |
| 2',6'-Dmt | D-Arg | 2',6'-Dmt | Dab | NH₂ |
| 2',6'-Dmt | D-Arg | 2',6'-Dmt | Dap | NH₂ |
| 3',5'-Dmt | D-Arg | 3',5'-Dmt | Arg | NH₂ |
| 3',5'-Dmt | D-Arg | 3',5'-Dmt | Lys | NH₂ |
| 3',5'-Dmt | D-Arg | 3',5'-Dmt | Orn | NH₂ |
| 3',5'-Dmt | D-Arg | 3',5'-Dmt | Dab | NH₂ |
| Tyr | D-Lys | Phe | Dap | NH₂ |
| Tyr | D-Lys | Phe | Arg | NH₂ |
| Tyr | D-Lys | Phe | Lys | NH₂ |
| Tyr | D-Lys | Phe | Orn | NH₂ |
| 2',6'-Dmt | D-Lys | Phe | Dab | NH₂ |
| 2',6'-Dmt | D-Lys | Phe | Dap | NH₂ |
| 2',6'-Dmt | D-Lys | Phe | Arg | NH₂ |
| 2',6'-Dmt | D-Lys | Phe | Lys | NH₂ |
| 3',5'-Dmt | D-Lys | Phe | Orn | NH₂ |
| 3',5'-Dmt | D-Lys | Phe | Dab | NH₂ |
| 3',5'-Dmt | D-Lys | Phe | Dap | NH₂ |
| 3',5'-Dmt | D-Lys | Phe | Arg | NH₂ |
| Tyr | D-Lys | Tyr | Lys | NH₂ |
| Tyr | D-Lys | Tyr | Orn | NH₂ |
| Tyr | D-Lys | Tyr | Dab | NH₂ |
| Tyr | D-Lys | Tyr | Dap | NH₂ |
| 2',6'-Dmt | D-Lys | Tyr | Lys | NH₂ |
| 2',6'-Dmt | D-Lys | Tyr | Orn | NH₂ |
| 2',6'-Dmt | D-Lys | Tyr | Dab | NH₂ |
| 2',6'-Dmt | D-Lys | Tyr | Dap | NH₂ |
| 2',6'-Dmt | D-Lys | 2',6'-Dmt | Lys | NH₂ |
| 2',6'-Dmt | D-Lys | 2',6'-Dmt | Orn | NH₂ |
| 2',6'-Dmt | D-Lys | 2',6'-Dmt | Dab | NH₂ |
| 2',6'-Dmt | D-Lys | 2',6'-Dmt | Dap | NH₂ |
| 2',6'-Dmt | D-Arg | Phe | dnsDap | NH₂ |
| 2',6'-Dmt | D-Arg | Phe | atnDap | NH₂ |
| 3',5'-Dmt | D-Lys | 3',5'-Dmt | Lys | NH₂ |
| 3',5'-Dmt | D-Lys | 3',5'-Dmt | Orn | NH₂ |
| 3',5'-Dmt | D-Lys | 3',5'-Dmt | Dab | NH₂ |
| 3',5'-Dmt | D-Lys | 3',5'-Dmt | Dap | NH₂ |
| Tyr | D-Lys | Phe | Arg | NH₂ |
| Tyr | D-Orn | Phe | Arg | NH₂ |
| Tyr | D-Dab | Phe | Arg | NH₂ |
| Tyr | D-Dap | Phe | Arg | NH₂ |
| 2',6'-Dmt | D-Arg | Phe | Arg | NH₂ |
| 2',6'-Dmt | D-Lys | Phe | Arg | NH₂ |
| 2',6'-Dmt | D-Orn | Phe | Arg | NH₂ |
| 2',6'-Dmt | D-Dab | Phe | Arg | NH₂ |
| 3',5'-Dmt | D-Dap | Phe | Arg | NH₂ |
| 3',5'-Dmt | D-Arg | Phe | Arg | NH₂ |
| 3',5'-Dmt | D-Lys | Phe | Arg | NH₂ |
| 3',5'-Dmt | D-Orn | Phe | Arg | NH₂ |
| Tyr | D-Lys | Tyr | Arg | NH₂ |
| Tyr | D-Orn | Tyr | Arg | NH₂ |
| Tyr | D-Dab | Tyr | Arg | NH₂ |
| Tyr | D-Dap | Tyr | Arg | NH₂ |
| 2',6'-Dmt | D-Arg | 2',6'-Dmt | Arg | NH₂ |
| 2',6'-Dmt | D-Lys | 2',6'-Dmt | Arg | NH₂ |
| 2',6'-Dmt | D-Orn | 2',6'-Dmt | Arg | NH₂ |
| 2',6'-Dmt | D-Dab | 2',6'-Dmt | Arg | NH₂ |
| 3',5'-Dmt | D-Dap | 3',5'-Dmt | Arg | NH₂ |
| 3',5'-Dmt | D-Arg | 3',5'-Dmt | Arg | NH₂ |
| 3',5'-Dmt | D-Lys | 3',5'-Dmt | Arg | NH₂ |
| 3',5'-Dmt | D-Orn | 3',5'-Dmt | Arg | NH₂ |
| Mmt | D-Arg | Phe | Lys | NH₂ |
| Mmt | D-Arg | Phe | Orn | NH₂ |
| Mmt | D-Arg | Phe | Dab | NH₂ |
| Mmt | D-Arg | Phe | Dap | NH₂ |
| Tmt | D-Arg | Phe | Lys | NH₂ |
| Tmt | D-Arg | Phe | Orn | NH₂ |
| Tmt | D-Arg | Phe | Dab | NH₂ |
| Tmt | D-Arg | Phe | Dap | NH₂ |
| Hmt | D-Arg | Phe | Lys | NH₂ |
| Hmt | D-Arg | Phe | Orn | NH₂ |
| Hmt | D-Arg | Phe | Dab | NH₂ |
| Hmt | D-Arg | Phe | Dap | NH₂ |
| Mmt | D-Lys | Phe | Lys | NH₂ |
| Mmt | D-Lys | Phe | Orn | NH₂ |
| Mmt | D-Lys | Phe | Dab | NH₂ |
| Mmt | D-Lys | Phe | Dap | NH₂ |
| Mmt | D-Lys | Phe | Arg | NH₂ |
| Tmt | D-Lys | Phe | Lys | NH₂ |
| Tmt | D-Lys | Phe | Orn | NH₂ |
| Tmt | D-Lys | Phe | Dab | NH₂ |
| Tmt | D-Lys | Phe | Dap | NH₂ |

TABLE 7-continued

Peptide Analogs with Mu-Opioid Activity

| Amino Acid Position 1 | Amino Acid Position 2 | Amino Acid Position 3 | Amino Acid Position 4 | C-Terminal Modification |
|---|---|---|---|---|
| Tmt | D-Lys | Phe | Arg | NH$_2$ |
| Hmt | D-Lys | Phe | Lys | NH$_2$ |
| Hmt | D-Lys | Phe | Orn | NH$_2$ |
| Hmt | D-Lys | Phe | Dab | NH$_2$ |
| Hmt | D-Lys | Phe | Dap | NH$_2$ |
| Hmt | D-Lys | Phe | Arg | NH$_2$ |
| Mmt | D-Lys | Phe | Arg | NH$_2$ |
| Mmt | D-Orn | Phe | Arg | NH$_2$ |
| Mmt | D-Dab | Phe | Arg | NH$_2$ |
| Mmt | D-Dap | Phe | Arg | NH$_2$ |
| Mmt | D-Arg | Phe | Arg | NH$_2$ |
| Tmt | D-Lys | Phe | Arg | NH$_2$ |
| Tmt | D-Orn | Phe | Arg | NH$_2$ |
| Tmt | D-Dab | Phe | Arg | NH$_2$ |
| Tmt | D-Dap | Phe | Arg | NH$_2$ |
| Tmt | D-Arg | Phe | Arg | NH$_2$ |
| Hmt | D-Lys | Phe | Arg | NH$_2$ |
| Hmt | D-Orn | Phe | Arg | NH$_2$ |
| Hmt | D-Dab | Phe | Arg | NH$_2$ |
| Hmt | D-Dap | Phe | Arg | NH$_2$ |
| Hmt | D-Arg | Phe | Arg | NH$_2$ |

Dab = diaminobutyric
Dap = diaminopropionic acid
Dmt = dimethyltyrosine
Mmt = 2'-methyltyrosine
Tmt = N,2',6'-trimethyltyrosine
Hmt = 2'-hydroxy,6'-methyltyrosine
dnsDap = β-dansyl-L-α,β-diaminopropionic acid
atnDap = β-anthraniloyl-L-α,β-diaminopropionic acid
Bio = biotin Examples of peptides that do not activate mu-opioid receptors include, but are not limited to, the aromatic-cationic peptides shown in Table 8.

TABLE 8

Peptide Analogs Lacking Mu-Opioid Activity

| Amino Acid Position 1 | Amino Acid Position 2 | Amino Acid Position 3 | Amino Acid Position 4 | C-Terminal Modification |
|---|---|---|---|---|
| D-Arg | Dmt | Lys | Phe | NH$_2$ |
| D-Arg | Dmt | Phe | Lys | NH$_2$ |
| D-Arg | Phe | Lys | Dmt | NH$_2$ |
| D-Arg | Phe | Dmt | Lys | NH$_2$ |
| D-Arg | Lys | Dmt | Phe | NH$_2$ |
| D-Arg | Lys | Phe | Dmt | NH$_2$ |
| Phe | Lys | Dmt | D-Arg | NH$_2$ |
| Phe | Lys | D-Arg | Dmt | NH$_2$ |
| Phe | D-Arg | Phe | Lys | NH$_2$ |
| Phe | D-Arg | Dmt | Lys | NH$_2$ |
| Phe | D-Arg | Lys | Dmt | NH$_2$ |
| Phe | Dmt | D-Arg | Lys | NH$_2$ |
| Phe | Dmt | Lys | D-Arg | NH$_2$ |
| Lys | Phe | D-Arg | Dmt | NH$_2$ |
| Lys | Phe | Dmt | D-Arg | NH$_2$ |
| Lys | Dmt | D-Arg | Phe | NH$_2$ |
| Lys | Dmt | Phe | D-Arg | NH$_2$ |
| Lys | D-Arg | Phe | Dmt | NH$_2$ |
| Lys | D-Arg | Dmt | Phe | NH$_2$ |
| D-Arg | Dmt | D-Arg | Phe | NH$_2$ |
| D-Arg | Dmt | D-Arg | Dmt | NH$_2$ |
| D-Arg | Dmt | D-Arg | Tyr | NH$_2$ |
| D-Arg | Dmt | D-Arg | Trp | NH$_2$ |
| Trp | D-Arg | Phe | Lys | NH$_2$ |
| Trp | D-Arg | Tyr | Lys | NH$_2$ |
| Trp | D-Arg | Trp | Lys | NH$_2$ |
| Trp | D-Arg | Dmt | Lys | NH$_2$ |
| D-Arg | Trp | Lys | Phe | NH$_2$ |
| D-Arg | Trp | Phe | Lys | NH$_2$ |
| D-Arg | Trp | Lys | Dmt | NH$_2$ |
| D-Arg | Trp | Dmt | Lys | NH$_2$ |
| D-Arg | Lys | Trp | Phe | NH$_2$ |
| D-Arg | Lys | Trp | Dmt | NH$_2$ |
| Cha | D-Arg | Phe | Lys | NH$_2$ |
| Ala | D-Arg | Phe | Lys | NH$_2$ |

Cha = cyclohexyl alanine

The amino acids of the peptides shown in Table 5 and 6 may be in either the L- or the D-configuration.

The peptides may be synthesized by any of the methods well known in the art. Suitable methods for chemically synthesizing the protein include, for example, those described by Stuart and Young in *Solid Phase Peptide Synthesis*, Second Edition, Pierce Chemical Company (1984), and in *Methods Enzymol.*, 289, Academic Press, Inc., New York (1997).

Alport Syndrome

Alport Syndrome is a genetic condition characterized by kidney disease, hearing loss, and eye abnormalities and occurs in approximately 1 in 50,000 newborns.

Mutations in the COL4A3, COL4A4, and COL4A5 genes cause Alport Syndrome. These genes each provide instructions for making one component of a protein called type IV collagen. This protein plays an important role in the kidneys, specifically in structures called glomeruli. Glomeruli are clusters of specialized blood vessels that remove water and waste products from blood and create urine. Mutations in these genes result in abnormalities of the type IV collagen in glomeruli, which prevents the kidneys from properly filtering the blood and allows blood and protein to pass into the urine. Gradual scarring of the kidneys occurs, eventually leading to progressive loss of kidney function and end-stage renal disease in many people with Alport Syndrome.

Type IV collagen is also an important component of inner ear structures, particularly the organ of Corti, that transform sound waves into nerve impulses for the brain. Alterations in type IV collagen often result in abnormal inner ear function during late childhood or early adolescence, which can lead to sensorineural deafness. In the eye, type IV collagen is important for maintaining the shape of the lens and the normal color of the retina. Mutations that disrupt type IV collagen can result in misshapen lenses (anterior lenticonus) and an abnormally colored retina. Significant hearing loss, eye abnormalities, and progressive kidney disease are more common in males with Alport Syndrome than in affected females.

Inheritance Patterns of Alport Syndrome

Alport Syndrome can have different inheritance patterns that are dependent on the genetic mutation.

About 80 percent of cases are caused by mutations in the COL4A5 gene and are inherited in an X-linked pattern. This gene is located on the X chromosome, which is one of the two sex chromosomes. In males (who have only one X chromosome), one altered copy of the COL4A5 gene in each cell is sufficient to cause kidney failure and other severe symptoms of the disorder. Boys with X-linked Alport Syndrome develop kidney failure by the teenage years or early adulthood, but the onset of kidney failure can be delayed until 40 to 50 years of age in some patients. In females (who have two X chromosomes), a mutation in one copy of the COL4A5 gene usually only results in hematuria, but some women experience more severe symptoms. As women with X-linked Alport Syndrome age, the risk of kidney failure increases.

In approximately 15 percent of cases, Alport Syndrome results from mutations in both copies of the COL4A3 or COL4A4 genes (which are located on chromosome 2) and is inherited in an autosomal recessive pattern. The parents of an individual with the autosomal recessive form of this condition each have one copy of the mutated gene and are called carriers. Some carriers are unaffected and others develop a less severe condition called thin basement membrane nephropathy, which is characterized by hematuria. Patients with the autosomal recessive form of Alport Syndrome will develop kidney failure by their teens or young adult years.

Alport Syndrome has autosomal dominant inheritance in about 5 percent of cases. People with this form of Alport Syndrome have one mutation in either the COL4A3 or COL4A4 gene in each cell. The clinical features of autosomal dominant Alport Syndrome are similar to those of X-linked disease. However, deterioration of renal function tends to occur more slowly. It remains unclear why some individuals with one mutation in the COL4A3 or COL4A4 gene have autosomal dominant Alport Syndrome and others have thin basement membrane nephropathy. Patients with autosomal dominant Alport Syndrome are usually well into middle age before kidney failure develops.

Clinical Manifestations

In general, Alport Syndrome is characterized by genetically determined dysfunction of the glomerular filter, mainly caused by mutations in the collagens assembling the GBM. Mice lacking the α3 chain of collagen IV (Col4a3$^{-/-}$) develop progressive glomerular damage. It is believed that podocytes fail to synthesize normal GBM, leaving the collagen IV network unstable and readily degradable. Podocytes are highly differentiated glomerular epithelial cells that play an important role in the maintenance of glomerular structure and function. Podocytes are integrated parts of the glomerular barrier and play a key role in preventing leakage of large molecules. Podocyte injury leads to proteinuria.

The earliest sign of GBM filter dysfunction is hematuria followed by albuminuria and subsequent nonselective proteinuria in increasing magnitude. The urine of Alport Syndrome patients often shows cylindruria and leukocyturia. Ultimately, not the GBM damage per se but the pro-inflammatory and pro-fibrotic consequences both in the tubulointerstitium and in the glomeruli resulting from progressive proteinuria, eventually lead to the development of end-stage kidney disease.

Overt proteinuria is typically absent in infant males with X-linked Alport Syndrome (XLAS). Age at identification of overt proteinuria shows interfamilial variability and ranges from early childhood to adolescence. In dogs with XLAS, a period of microalbuminuria precedes the development of overt proteinuria and quantitative increases in interstitial volume due to tubular atrophy and fibrosis. Dogs with XLAS exhibit increased proximal tubular epithelial cell uptake of albumin, a process that has been linked to cellular injury. Preliminary data from the Alport Syndrome Treatments and Outcomes Registry (ASTOR) indicates that boys with Alport Syndrome also exhibit a transitional stage of microalbuminuria before overt proteinuria becomes established.

Measurements of cortical interstitial volumes in Alport Syndrome males have shown that interstitial fibrosis is unusual before age 10. Cortical interstitial volumes become abnormal in many Alport Syndrome males during the second decade of life, and are inversely correlated with glomerular filtration rates. These observations suggest that, as in other chronic glomerulopathies, interstitial fibrosis is a significant contributor to loss of renal function, and prevention of interstitial fibrosis in Alport Syndrome males may require intervention during childhood.

Normal glomerular capillaries filter plasma through a basement membrane rich in the alpha-3, alpha-4, and alpha-5 chains of type IV collagen. These 3 isoforms are absent biochemically from the glomeruli of patients with XLAS. Instead, their GBMs retain a fetal distribution of the alpha-1 and alpha-2 isoforms of type IV collagen because they fail to switch their alpha-chain use developmentally. The anomalous persistence of these fetal isoforms in the GBM confers an increase in susceptibility to proteolytic attack by collagenases and cathepsins. Thus, the incorporation of the cysteine-rich alpha-3, alpha-4, and alpha-5 chains into specialized basement membranes like the GBM may have evolved to enhance their resistance to proteolytic degradation at the site of glomerular filtration. The absence of these potentially protective collagen IV isoforms in GBM from XLAS patients may explain the progressive basement membrane splitting and increased damage as the kidneys deteriorate in these patients.

Hypertension is usually detectable by the second decade of life and typically manifests in XLAS males as well as autosomal recessive and autosomal dominant Alport Syndrome patients. Edema and nephrotic syndrome are present in 30-40% of young adults with Alport syndrome; they are not common in early childhood, but their incidence progressively increases with age. With the onset of renal insufficiency, symptoms of chronic anemia and osteodystrophy may become evident.

Several specific ocular anomalies can occur in patients with Alport Syndrome, including anterior lenticonus, posterior polymorphous corneal dystrophy, recurrent corneal erosion, temporal macular thinning, cataracts, lacrimation, photophobia, vision loss, keratoconus, and dot-and-fleck retinopathy. Some patients with anterior lenticonus develop refractive errors in late adolescence or adulthood; cataract removal may be necessary in some adult patients.

Other clinical manifestations also include individually variable progressive glomerulosclerosis, uraemia, macro-thrombocytopenia, glomerulonephritis, bilateral sensorineural deafness, GBM ultrastructural abnormalities (e.g., accumulation of glomerular matrix, elevated MMP-9 levels in mesangial cells), and diffuse leiomyomatosis of esophagus or female genitalia.

Pathogenesis

FIG. 1 shows the 5 stages of Alport nephropathy. Stage 1 of the Alport nephropathy begins at birth and is associated with predominantly thin and presumably fragile GBMs. The transition from stage 1 to stage 2 occurs with the onset of microalbuminuria, arbitrarily defined as a microalbumin-creatinine ratio greater than 30 mg/g. The urine dipstick typically remains negative for albumin until the microalbumin-creatinine ratio increases to about 200 mg/g creatinine. Once there is overt proteinuria, defined as a urine dipstick reading for protein of 1+ or greater, or a urine protein-creatinine ratio greater than 0.2 mg/mg, the patient has moved into stage 3. The histological correlates of stages 2 and 3 include thickening and lamellation of GBMs associated with effacement of visceral epithelial cell (podocyte) foot processes. Glomerular filtration rate begins to decline in stage 4. Glomerular filtration rate, as estimated by creatinine clearance is inversely correlated with cortical interstitial volume fraction, a measure of fibrosis of the renal interstitium. Creatinine clearance is maintained in the normal range until cortical interstitial fibrosis increases above the upper limit of the normal range, suggesting that suppression of renal interstitial fibrosis will protect kidney function in Alport patients. In boys with Alport syndrome, cortical interstitial volume fraction is usually normal through the first 10 years of life but then begins to increase.

Overall, about 50% of males with XLAS reach stage 5 end-stage renal disease by age 25 years, 90% by age 40 years, and nearly 100% by age 60 years. The timing of stage 5 in men with XLAS is heavily influenced by COL4A5 genotype: those with deletion and nonsense mutations progress through the above stages relatively rapidly, while those with missense mutations often progress at a slower pace. Approximately 30% of females with X-linked Alport syndrome reach end-stage renal disease by age 80 years.

Diagnosis

Early and accurate diagnosis is a prerequisite for early intervention in Alport Syndrome. The diagnostic approach in subjects with hematuria is based on careful evaluation of clinical features and family history, supplemented by tissue biopsy and molecular genetic analysis. Hematuria is present in Alport Syndrome long before hearing loss and ocular abnormalities are detectable. Therefore, while the presence of characteristic sensorineural deafness or ocular changes in a subject with hematuria increases suspicion for Alport Syndrome, normal hearing and eye examinations do not serve to rule out Alport Syndrome. A suspected diagnosis of Alport Syndrome can be confirmed by biopsy of the kidney or skin. Complete evaluation of kidney biopsy material requires light, immunofluorescence, and electron microscopy.

Diagnosis of Alport Syndrome is made on the basis of pathognomonic changes in GBM ultrastructure and abnormalities of renal basement membrane expression of type IV collagen chains. The alpha3, alpha4, and alpha5 chains of type IV collagen are present in the GBM of normal individuals. In XLAS subjects, however, the presence of the dysfunctional alpha5 chain causes the assembly of the entire collagen IV complex to fail, and none of these three chains are detectable in either the glomerular or the renal tubular basement membrane. XLAS can also be diagnosed by immunostaining of skin biopsy specimens for type IV collagen. Specifically, only alpha5 is normally expressed in the skin, so the hallmark of XLAS on a skin biopsy is the absence of alpha5 staining.

Standard diagnostic tests thus include a combination of urinalysis (for detecting hematuria and proteinuria), hematologic studies (for assessing renal insufficiency), kidney or skin biopsy (for evaluating ultrastructural abnormalities), genetic testing (for mutations in COL4A3, COL4A4 or COL4A5), audiometry (for detecting sensorineural deafness), ophthalmic examination (for detecting and monitoring anterior lenticonus, keratoconus, cataracts, posterior polymorphous corneal dystrophy, retinal flecks and other eye lesions), and renal ultrasonography. Gregory et al., *Contrib Nephrol*, 117: 1-28 (1996) provides the following 10 criteria, of which 4 must be met for the diagnosis of Alport Syndrome:

Family history of nephritis of unexplained hematuria in a first degree relative of the index case or in a male relative linked through any numbers of females;
Persistent hematuria without evidence of another possibly inherited nephropathy such as thin glomerular basement membrane disease, polycystic kidney disease or IgA nephropathy;
Bilateral sensorineural deafness in the 2000 to 8000 Hz range. Hearing loss develops gradually, is not present in early infancy and commonly presents before the age of 30 years;
A mutation in COL4A3, COL4A4 or COL4A5;
Immunohistochemical evidence of complete or partial lack of the Alport epitope in glomerular, or epidermal basement membranes, or both;
Widespread GBM ultrastructural abnormalities, in particular thickening, thinning and splitting;
Eye lesions including anterior lenticonus, keratoconus, posterior subcapsular cataract, posterior polymorphous dystrophy and retinal flecks;
Gradual progression to end-stage kidney disease in the index case of at least two family members;
Macrothrombocytopenia or granulocytic inclusions, similar to the May-Hegglin anomaly; and
Diffuse leiomyomatosis of esophagus or female genitalia, or both.

Alport Syndrome patients also show aberrant urine levels of ADAM8, fibronectin, myosin 10, MMP-2, MMP-9, and podocin compared to a normal control subject. Additionally, levels of various biomarker combinations in urine are significantly different between Alport Syndrome patients and healthy subjects. For example, several combinations of three (fibronectin, myosin 10, and MMP-2 or MMP-9) and two (myosin 10, and MMP-2 or MMP-9) parameters significantly discriminate between healthy controls and Alport Syndrome patients, thus permitting early diagnosis of Alport Syndrome.

Current Treatments

ACE inhibitors or ARBs are generally administered to patients with Alport Syndrome who have proteinuria with or without hypertension. Both classes of drugs apparently help to reduce proteinuria by decreasing intraglomerular pressure. Moreover, by inhibiting angiotensin II, a growth factor that is implicated in glomerular sclerosis, these drugs have a potential role in slowing sclerotic progression. ARBs that have been used to treat Alport Syndrome patients include, but are not limited to losartan, candesartan, valsartan, eprosartan, telmisartan, and irbesartan. Examples of ACE inhibitors include captopril, alacepril, lisinopril, imidapril, quinapril, temocapril, delapril, benazepril, cilazapril, trandolapril, enalapril, ceronapril, fosinopril, imadapril, mobertpril, perindopril, ramipril, spirapril, and randolapril. ACE inhibitors are usually not prescribed for pregnant patients because they may cause birth defects. The most common side effects are cough, elevated blood potassium levels, low blood pressure, dizziness, headache, drowsiness, weakness, abnormal taste (metallic or salty taste), and rash. The most serious, but rare, side effects of ACE inhibitors are kidney failure, allergic reactions, a decrease in white blood cells, and swelling of tissues (angioedema).

Therapeutic intervention in renal failure may also be achieved by administering HMG-CoA reductase inhibitors, aldosterone inhibitors, aliskiren, calcineurin inhibitors (e.g., cyclosporine A, tacrolimus), endothelin receptor antagonists (e.g., sitaxentan, ambrisentan (LETAIRIS), atrasentan, BQ-123, zibotentan, bosentan (TRACLEER), macitentan, tezosentan, BQ-788 and A192621), sulodexide, vasopeptidase inhibitors (e.g., AVE7688), anti-transforming growth factor-β1 antibody, chemokine receptor 1 blockers, bone morphogenetic protein-7, PPARγ agonists (e.g., rosiglitazone, pioglitazone, MRL24, Fmoc-L-Leu, SR1664, SR1824, GW0072, MCC555, CLX-0921, PAT5A, L-764406, nTZDpa, CDDO (2-cyano-3,12-dioxooleana-1,9-dien-28- oic acid), ragaglitazar, O-arylmandelic acids, and NSAIDs) and matrix metalloproteinase inhibitors (e.g., BAY-12-9566).

Examples of HMG-CoA reductase inhibitors include, but are not limited to, lovastatin (e.g., ADVICOR® (niacin extended-release/lovastatin) (AbbVie Pharmaceuticals, Chicago, Ill.), ALTOPREV™ (lovastatin extended-release) (Shiongi, Inc., Atlanta, Ga.), MEVACOR® (Merck, Whitehouse Station, N.J.), atorvastatin (e.g., CADUET® (amlodipine and atorvastatin) (Pfizer, Morrisville, Pa.), LIPITOR® (Pfizer, Morrisville, Pa.)), rosuvastatin and/or rosuvastatin calcium (e.g., CRESTOR® (AstraZeneca, London, England)), simvastatin (e.g., JUVISYNC® (sitagliptin/simvastatin) (Merck, Whitehouse Station, N.J.)), SIMCOR® (niacin extended-release/simvastatin) (AbbVie Pharmaceuticals, Chicago, Ill.), VYTORIN® (ezetimibe/simvastatin) (Merck, Whitehouse Station, N.J.), and ZOCOR® (Merck, Whitehouse Station, N.J.)), fluvastatin and/or fluvastatin sodium (e.g., LESCOL®, LESCOL XL (fluvastatin extended-release) (Mylan Pharmaceuticals, Morgantown, W. Va.)), pitavastatin (e.g., LIVALO® (Kowa Pharmaceuticals, Montgomery, Ala.)), pravastatin and/or pravastatin sodium (e.g., PRAVACHOL® (Bristol-Myers Squibb, New York, N.Y.)).

Aldosterone inhibitors include spironolactone (Aldactone®), eplerenone (Inspra®), canrenone (canrenoate potassium), prorenone (prorenoate potassium), and mexrenone (mexrenoate potassium).

Kidney transplantation is usually offered to patients with Alport Syndrome who develop end-stage renal disease (ESRD). Recurrent disease does not occur in the transplanted kidney, and the allograft survival rate in these patients is similar to that in patients with other renal diseases. However, anti-glomerular basement membrane (anti-GBM) nephritis develops in a small percentage of transplant patients with Alport Syndrome.

Therapeutic Methods

The following discussion is presented by way of example only, and is not intended to be limiting.

One aspect of the present technology includes methods of treating a disease or condition characterized by a reduction of function, decreased expression level of, and/or deficiency in one or more of COL4A3, COL4A4 and COL4A5 genes. Additionally or alternatively, in some embodiments, the present technology includes methods of treating Alport Syndrome. In some embodiments, the subject is diagnosed as having, suspected as having, or at risk of having a disease or condition characterized by a reduction of function, decreased expression level of, and/or deficiency in one or more of COL4A3, COL4A4 and COL4A5 genes. Additionally or alternatively, in some embodiments, the subject is diagnosed as having Alport Syndrome. In therapeutic applications, compositions or medicaments comprising an aromatic-cationic peptide, such as D-Arg-2',6'-Dmt-Lys-Phe-$NH_2$, or a pharmaceutically acceptable salt thereof, such as acetate, tartrate, or trifluoroacetate salt, are administered to a subject suspected of, or already suffering from such a disease or condition (such as, e.g., subjects exhibiting aberrant levels and/or function of one or more of ADAM8, fibronectin, myosin 10, MMP-2, MMP-9, and podocin compared to a normal control subject, and/or a subject diagnosed with a disease or condition characterized by a reduction of function, decreased expression level of, and/or deficiency in one or more of COL4A3, COL4A4 and COL4A5 genes, and/or a subject diagnosed with Alport Syndrome), in an amount sufficient to cure, or at least partially arrest, the symptoms of the disease, including its complications and intermediate pathological phenotypes in development of the disease.

Subjects suffering from a disease or condition characterized by a reduction of function, decreased expression level of, and/or deficiency in one or more of COL4A3, COL4A4 and COL4A5 genes and/or subjects suffering from Alport syndrome can be identified by any or a combination of diagnostic or prognostic assays known in the art. For example, typical symptoms of Alport Syndrome include, but are not limited to, hematuria, proteinuria, cylindruria, leukocyturia, hypertension, edema, microalbuminuria, declining glomerular filtration rate, interstitial fibrosis, interstitial inflammation, tubular damage, GBM ultrastructural abnormalities, nephrotic syndrome, glomerulonephritis, end-stage kidney disease, chronic anemia, macrothrombocytopenia, osteodystrophy, sensorineural deafness, anterior lenticonus, dot-and-fleck retinopathy, posterior polymorphous corneal dystrophy, recurrent corneal erosion, temporal macular thinning, cataracts, lacrimation, photophobia, vision loss, keratoconus, and leiomyomatosis.

In some embodiments, the subject may exhibit aberrant levels or function of one or more of ADAM8, fibronectin, myosin 10, MMP-2, MMP-9, and podocin compared to a normal control subject, which is measurable using techniques known in the art. In some embodiments, the subject may exhibit one or more mutations in COL4A3, COL4A4, and COL4A5, which are involved in the production or assembly of type IV collagen fibers and are detectable using techniques known in the art.

In some embodiments, subjects with a disease or condition characterized by a reduction of function, decreased expression level of, and/or deficiency in one or more of COL4A3, COL4A4 and COL4A5 genes, and/or subjects suffering from Alport Syndrome that are treated with the aromatic-cationic peptide will show amelioration or elimination of one or more of the following symptoms: hematuria, proteinuria, cylindruria, leukocyturia, hypertension, edema, microalbuminuria, declining glomerular filtration rate, interstitial fibrosis, interstitial inflammation, tubular damage, GBM ultrastructural abnormalities, nephrotic syndrome, glomerulonephritis, end-stage kidney disease, chronic anemia, macrothrombocytopenia, osteodystrophy, sensorineural deafness, anterior lenticonus, dot-and-fleck retinopathy, posterior polymorphous corneal dystrophy, recurrent corneal erosion, temporal macular thinning, cataracts, lacrimation, photophobia, vision loss, keratoconus, and leiomyomatosis. In certain embodiments, subjects with a disease or condition characterized by a reduction of function, decreased expression level of, and/or deficiency in one or more of COL4A3, COL4A4 and COL4A5 genes, and/or Alport Syndrome that are treated with the aromatic-cationic peptide will show normalization of one or more of ADAM8, fibronectin, myosin 10, MMP-2, MMP-9, and podocin urine levels by at least 10% compared to untreated Alport Syndrome subjects. In certain embodiments, subjects with a disease or condition characterized by a reduction of function, decreased expression level of, and/or deficiency in one or more of COL4A3, COL4A4 and COL4A5 genes and/or a subject suffering from Alport Syndrome that are treated with the aromatic-cationic peptide will show MMP-9 expression levels in mesangial cells that are similar to that observed in a normal control subject.

Prophylactic Methods

In one aspect, the present technology provides a method for preventing or delaying the onset of a disease or condition characterized by a reduction of function, decreased expression level of, and/or deficiency one or more of COL4A3, COL4A4 and COL4A5 genes. Additionally or alternatively, in some aspects, the present technology provides a method for preventing or delaying the onset Alport Syndrome.

Subjects at risk for aberrant levels and/or function of one or more of ADAM8, fibronectin, myosin 10, MMP-2, MMP-9, and podocin compared to a normal control subject, include those at risk or susceptible to a disease or condition characterized by a reduction of function, decreased expression level of, and/or deficiency in one or more of COL4A3, COL4A4 and COL4A5 genes, and/or a subject at risk or susceptible to Alport Syndrome. Such subjects can be identified by, e.g., any or a combination of diagnostic or prognostic assays known in the art. In prophylactic applications, pharmaceutical compositions or medicaments of aromatic-cationic peptides, such as D-Arg-2',6'-Dmt-Lys-Phe-NH$_2$, or a pharmaceutically acceptable salt thereof, such as acetate, tartrate, or trifluoroacetate salt, are administered to a subject susceptible to, or otherwise at risk of a disease or condition characterized by a reduction of function, decreased expression level of, and/or deficiency in one or more of COL4A3, COL4A4 and COL4A5 genes, and/or a subject susceptible to, or otherwise at risk of Alport Syndrome, in an amount sufficient to eliminate or reduce the risk, or delay the onset of the disease, including biochemical, histologic and/or behavioral symptoms of the disease, its complications and intermediate pathological phenotypes presenting during development of the disease. Administration of a prophylactic aromatic-cationic peptide can occur prior to the manifestation of symptoms characteristic of the disease or disorder, such that the disease or disorder is prevented or, alternatively, delayed in its progression.

In some embodiments, subjects at risk for aberrant levels and/or function of one or more of ADAM8, fibronectin, myosin 10, MMP-2, MMP-9, and podocin compared to a normal control subject, are those at risk for, or susceptible to a disease or condition characterized by a reduction of function, decreased expression level of, and/or deficiency in one or more of COL4A3, COL4A4 and COL4A5 genes, and/or a subjects at risk for or susceptible to Alport Syndrome.

For therapeutic and/or prophylactic applications, a composition comprising an aromatic-cationic peptide, such as D-Arg-2',6'-Dmt-Lys-Phe-NH$_2$, or a pharmaceutically acceptable salt thereof, such as acetate, tartrate, or trifluoroacetate salt, is administered to the subject. In some embodiments, the peptide composition is administered one, two, three, four, or five times per day. In some embodiments, the peptide composition is administered more than five times per day. Additionally or alternatively, in some embodiments, the peptide composition is administered every day, every other day, every third day, every fourth day, every fifth day, or every sixth day. In some embodiments, the peptide composition is administered weekly, bi-weekly, tri-weekly, or monthly. In some embodiments, the peptide composition is administered for a period of one, two, three, four, or five weeks. In some embodiments, the peptide is administered for six weeks or more. In some embodiments, the peptide is administered for twelve weeks or more. In some embodiments, the peptide is administered for a period of less than one year. In some embodiments, the peptide is administered for a period of more than one year. In some embodiments, the peptide is administered throughout the subject's life.

In some embodiments of the methods of the present technology, the aromatic-cationic peptide is administered daily for 1 week or more. In some embodiments of the methods of the present technology, the aromatic-cationic peptide is administered daily for 2 weeks or more. In some embodiments of the methods of the present technology, the aromatic-cationic peptide is administered daily for 3 weeks or more. In some embodiments of the methods of the present technology, the aromatic-cationic peptide is administered daily for 4 weeks or more. In some embodiments of the methods of the present technology, the aromatic-cationic peptide is administered daily for 6 weeks or more. In some embodiments of the methods of the present technology, the aromatic-cationic peptide is administered daily for 12 weeks or more. In some embodiments, the peptide is administered throughout the subject's life.

In some embodiments, treatment with the aromatic-cationic peptide will prevent or delay the onset of one or more of the following symptoms: hematuria, proteinuria, cylindruria, leukocyturia, hypertension, edema, microalbuminuria, declining glomerular filtration rate, interstitial fibrosis, interstitial inflammation, tubular damage, GBM ultrastructural abnormalities, nephrotic syndrome, glomerulonephritis, end-stage kidney disease, chronic anemia, macrothrombocytopenia, osteodystrophy, sensorineural deafness, anterior lenticonus, dot-and-fleck retinopathy, posterior polymorphous corneal dystrophy, recurrent corneal erosion, temporal macular thinning, cataracts, lacrimation, photophobia, vision loss, keratoconus, and leiomyomatosis. In certain embodiments, the urine levels of one or more of ADAM8, fibronectin, myosin 10, MMP-2, MMP-9, and podocin in subjects with a disease or condition characterized by a reduction of function, decreased expression level of, and/or deficiency in one or more of COL4A3, COL4A4 and COL4A5 genes, and/or in subjects having Alport Syndrome. In some embodiments, signs and symptoms of subjects treated with the aromatic-cationic peptide will resemble those observed in healthy controls. In certain embodiments, subjects with a disease or condition characterized by a reduction of function, decreased expression level of, and/or deficiency in one or more of COL4A3, COL4A4 and COL4A5 genes, and/or Alport Syndrome that are treated with the aromatic-cationic peptide will show MMP-9 expression in mesangial cells that is similar to that observed in a normal control subject.

Determination of the Biological Effect of the Aromatic-Cationic Peptide-Based Therapeutic In various embodiments, suitable in vitro or in vivo assays are performed to determine the effect of a specific aromatic-cationic peptide-based therapeutic and whether its administration is indicated for treatment. In various embodiments, in vitro assays can be performed with representative animal models, to determine if a given aromatic-cationic peptide-based therapeutic exerts the desired effect on reducing or eliminating signs and/or symptoms of a disease or condition characterized by a reduction of function, decreased expression level of, and/or deficiency in one or more of COL4A3, COL4A4 and COL4A5 genes, and/or having Alport Syndrome. Compounds for use in therapy can be tested in suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects. In some embodiments, in vitro or in vivo testing is directed to the biological function of D-Arg-2',6'-Dmt-Lys-Phe-NH$_2$, or a pharmaceutically acceptable salt thereof, such as acetate, tartrate, or trifluoroacetate salt.

Animal models of Alport Syndrome may be generated using techniques known in the art, including, for example by generating random or targeted mutations in one or more of COL4A3, COL4A4, and COL4A5. For example, murine models of X-linked Alport Syndrome and autosomal recessive Alport Syndrome have been generated by targeted disruption of the mouse Col4a5 gene and mouse Col4a3 gene respectively. See Rheault et al., *J Am Soc Nephrol.* 15(6):1466-74 (2004); Cosgrove et al., *Genes Dev.* 10(23): 2981-92 (1996). Such models may be used to demonstrate the biological effect of aromatic-cationic peptides of the present technology, such as D-Arg-2',6'-Dmt-Lys-Phe-NH$_2$, in the prevention and treatment of conditions arising from disruption of a particular gene, and for determining what comprises a therapeutically effective amount of peptide in a given context.

Modes of Administration and Effective Dosages

Any method known to those in the art for contacting a cell, organ or tissue with an aromatic-cationic peptide of the present technology, such as D-Arg-2',6'-Dmt-Lys-Phe-NH$_2$, or a pharmaceutically acceptable salt thereof, such as acetate, tartrate, or trifluoroacetate salt, may be employed. Suitable methods include in vitro, ex vivo, or in vivo methods. In vivo methods typically include the administration of an aromatic-cationic peptide, such as those described above, to a mammal, suitably a human. When used in vivo for therapy, the aromatic-cationic peptides, such as D-Arg-2',6'-Dmt-Lys-Phe-NH$_2$, or a pharmaceutically acceptable salt thereof, such as acetate, tartrate, or trifluoroacetate salt, are administered to the subject in effective amounts (i.e., amounts that have desired therapeutic effect). The dose and dosage regimen will depend upon the degree of the infection in the subject, the characteristics of the particular aromatic-cationic peptide used, e.g., its therapeutic index, the subject, and the subject's history.

The effective amount may be determined during preclinical trials and clinical trials by methods familiar to physicians and clinicians. An effective amount of a peptide useful in the methods may be administered to a mammal in need thereof by any of a number of well-known methods for administering pharmaceutical compounds. The peptide may be administered systemically or locally.

The peptide may be formulated as a pharmaceutically acceptable salt. The term "pharmaceutically acceptable salt" means a salt prepared from a base or an acid which is acceptable for administration to a patient, such as a mammal (e.g., salts having acceptable mammalian safety for a given dosage regime). However, it is understood that the salts are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a peptide contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucuronic, mandelic, mucic, nicotinic, orotic, pamoic, pantothenic, sulfonic acids (e.g., benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like. In some embodiments, the salt is an acetate, tartrate, or trifluoroacetate salt.

The aromatic-cationic peptides described herein, such as D-Arg-2',6'-Dmt-Lys-Phe-NH$_2$, or a pharmaceutically acceptable salt thereof, such as acetate, tartrate, or trifluoroacetate salt, can be incorporated into pharmaceutical compositions for administration, singly or in combination, to a subject for the treatment or prevention of a disorder described herein. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course (e.g., 7 days of treatment).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The aromatic-cationic peptide compositions can include a carrier, which can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, it will be advantageous to include isotonic agents, for example, sugars, polyalcohols such as mannitol, sorbitol, or sodium chloride in the composition. Prolonged absorption of the injectable compositions can be brought about by including in the composition an agent that delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressurized container or dispenser, which contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed by iontophoresis.

A therapeutic protein or peptide can be formulated in a carrier system. The carrier can be a colloidal system. The colloidal system can be a liposome, a phospholipid bilayer vehicle. In one embodiment, the therapeutic peptide is encapsulated in a liposome while maintaining peptide integrity. One skilled in the art would appreciate that there are a variety of methods to prepare liposomes. (See Lichtenberg, et al., *Methods Biochem. Anal.*, 33:337-462 (1988); Anselem, et al., *Liposome Technology*, CRC Press (1993)). Liposomal formulations can delay clearance and increase cellular uptake (See Reddy, *Ann. Pharmacother.*, 34(7-8): 915-923 (2000)). An active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In one embodiment, the therapeutic peptide can be embedded in the polymer matrix, while maintaining protein integrity. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, *Ann. Pharmacother.*, 34(7-8):915-923 (2000)). A polymer formulation for human growth hormone (hGH) has been used in clinical trials. (See Kozarich and Rich, *Chemical Biology*, 2:548-552 (1998)).

Examples of polymer microsphere sustained release formulations are described in PCT publication WO 99/15154 (Tracy, et al.), U.S. Pat. Nos. 5,674,534 and 5,716,644 (both to Zale, et al.), PCT publication WO 96/40073 (Zale, et al.), and PCT publication WO 00/38651 (Shah, et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The therapeutic compounds can also be formulated to enhance intracellular delivery. For example, liposomal delivery systems are known in the art, see, e.g., Chonn and Collis, "Recent Advances in Liposome Drug Delivery Systems," *Current Opinion in Biotechnology* 6:698-708 (1995); Weiner, "Liposomes for Protein Delivery: Selecting Manufacture and Development Processes," *Immunomethods*, 4(3): 201-9 (1994); and Gregoriadis, "Engineering Liposomes for Drug Delivery: Progress and Problems," *Trends Biotechnol.*, 13(12):527-37 (1995). Mizguchi, et al., *Cancer Lett.*, 100: 63-69 (1996), describes the use of fusogenic liposomes to deliver a protein to cells both in vivo and in vitro.

Dosage, toxicity and therapeutic efficacy of any therapeutic agent can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are advantageous. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds may be within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to determine useful doses in humans accurately. Levels in plasma may be measured, for example, by high performance liquid chromatography.

Typically, an effective amount of the aromatic-cationic peptides, sufficient for achieving a therapeutic or prophylactic effect, range from about 0.000001 mg per kilogram body weight per day to about 10,000 mg per kilogram body weight per day. Suitably, the dosage ranges are from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In one embodiment, a single dosage of peptide ranges from 0.001-10,000 micrograms per kg body weight. In one embodiment, aromatic-cationic peptide concentrations in a carrier range from 0.2 to 2000 micrograms per delivered milliliter. An exemplary treatment regime entails administration once per day or once a week. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regime.

In some embodiments, a therapeutically effective amount of an aromatic-cationic peptide may be defined as a concentration of peptide at the target tissue of $10^{-12}$ to $10^{-6}$ molar, e.g., approximately $10^{-7}$ molar. This concentration may be delivered by systemic doses of 0.001 to 100 mg/kg or equivalent dose by body surface area. The schedule of doses would be optimized to maintain the therapeutic concentration at the target tissue, such as by single daily or weekly administration, but also including continuous administration (e.g., parenteral infusion or transdermal application).

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The mammal treated in accordance with the present methods can be any mammal, including, for example, farm animals, such as sheep, pigs, cows, and horses; pet animals, such as dogs and cats; laboratory animals, such as rats, mice and rabbits. In some embodiments, the mammal is a human.

Combination Therapy with Aromatic-Cationic Peptides

In some embodiments, the aromatic-cationic peptides, such as D-Arg-2',6'-Dmt-Lys-Phe-NH$_2$, or a pharmaceutically acceptable salt thereof, such as acetate, tartrate, or trifluoroacetate salt, may be combined with one or more additional therapies for the prevention or treatment of a disease or condition characterized by a reduction of function, decreased expression level of, and/or deficiency in one or more of COL4A3, COL4A4 and COL4A5 genes, In some embodiments, the aromatic-cationic peptides, such as D-Arg-2',6'-Dmt-Lys-Phe-NH$_2$, or a pharmaceutically acceptable salt thereof, such as acetate, tartrate, or trifluoroacetate salt, may be combined with one or more additional therapies for the prevention or treatment of Alport Syndrome. Additional therapeutic agents include, but are not limited to, ACE inhibitors, ARBs, HMG-CoA reductase inhibitors, aldosterone inhibitors, aliskiren, calcineurin inhibitors (e.g., cyclosporine A, tacrolimus), endothelin receptor antagonists (e.g., sitaxentan, ambrisentan (LE-TAIRIS), atrasentan, BQ-123, zibotentan, bosentan (TRA-CLEER), macitentan, tezosentan, BQ-788 and A192621), sulodexide, vasopeptidase inhibitors (e.g., AVE7688), anti-transforming growth factor-β1 antibody, chemokine receptor 1 blockers, bone morphogenetic protein-7, PPARγ agonists (e.g., rosiglitazone, pioglitazone, MRL24, Fmoc-L-Leu, SR1664, SR1824, GW0072, MCC555, CLX-0921, PAT5A, L-764406, nTZDpa, CDDO (2-cyano-3,12-dioxooleana-1,9-dien-28-oic acid), ragaglitazar, O-arylmandelic acids, and NSAIDs) and BAY-12-9566.

In some embodiments, the ACE inhibitors are selected from the group consisting of captopril, alacepril, lisinopril, imidapril, quinapril, temocapril, delapril, benazepril, cilazapril, trandolapril, enalapril, ceronapril, fosinopril, imadapril, mobertpril, perindopril, ramipril, spirapril, randolapril and pharmaceutically acceptable salts of such compounds.

In some embodiments, the ARBs are selected from the group consisting of losartan, candesartan, valsartan, eprosartan, telmisartan, and irbesartan.

In some embodiments, the HMG-CoA reductase inhibitors (or statins) are selected from the group consisting of lovastatin (e.g., ADVICOR® (niacin extended-release/lovastatin) (AbbVie Pharmaceuticals, Chicago, Ill.), ALTOPREV™ (lovastatin extended-release) (Shiongi, Inc., Atlanta, Ga.), MEVACOR® (Merck, Whitehouse Station, N.J.), atorvastatin (e.g., CADUET® (amlodipine and atorvastatin) (Pfizer, Morrisville, Pa.), LIPITOR® (Pfizer, Morrisville, Pa.)), rosuvastatin and/or rosuvastatin calcium (e.g., CRESTOR® (AstraZeneca, London, England)), simvastatin (e.g., JUVISYNC® (sitagliptin/simvastatin) (Merck, Whitehouse Station, N.J.)), SIMCOR® (niacin extended-release/simvastatin) (AbbVie Pharmaceuticals, Chicago, Ill.), VYTORIN® (ezetimibe/simvastatin) (Merck, Whitehouse Station, N.J.), and ZOCOR® (Merck, Whitehouse Station, N.J.)), fluvastatin and/or fluvastatin sodium (e.g., LESCOL®, LESCOL XL (fluvastatin extended-release) (Mylan Pharmaceuticals, Morgantown, W. Va.)), pitavastatin (e.g., LIVALO® (Kowa Pharmaceuticals, Montgomery, Ala.)), pravastatin and pravastatin sodium (e.g., PRAVACHOL® (Bristol-Myers Squibb, New York, N.Y.)).

In some embodiments, the aldosterone inhibitors are selected from the group consisting of spironolactone (Aldactone®), eplerenone (Inspra®), canrenone (canrenoate potassium), prorenone (prorenoate potassium), and mexrenone (mexrenoate potassium).

In one embodiment, an additional therapeutic agent is administered to a subject in combination with an aromatic cationic peptide, such that a synergistic therapeutic effect is produced. For example, administration of the peptide with one or more additional therapeutic agents for the prevention or treatment of a disease or condition characterized by a reduction of function, decreased expression level of, and/or deficiency in one or more of COL4A3, COL4A4 and COL4A5 genes will have greater than additive effects in the prevention or treatment of the disease. Additionally or alternatively, in some embodiments, administration of the peptide with one or more additional therapeutic agents for the prevention or treatment of Alport Syndrome will have greater than additive effects in the prevention or treatment of the disease. For example, lower doses of one or more of therapeutic agents may be used in treating or preventing a disease or condition characterized by a reduction of function, decreased expression level of, and/or deficiency in one or more of COL4A3, COL4A4 and COL4A5 genes resulting in increased therapeutic efficacy and decreased side-effects. Additionally or alternatively, lower doses of one or more of therapeutic agents may be used in treating or preventing Alport Syndrome, resulting in increased therapeutic efficacy and decreased side-effects. In some embodiments, the peptide is administered in combination with one or more ACE inhibitors, ARBs, HMG-CoA reductase inhibitors, aldosterone inhibitors, aliskiren, calcineurin inhibitors (e.g., cyclosporine A, tacrolimus), endothelin receptor antagonists (e.g., sitaxentan, ambrisentan (LETAIRIS), atrasentan, BQ-123, zibotentan, bosentan (TRACLEER), macitentan, tezosentan, BQ-788 and A192621), sulodexide, vasopeptidase inhibitors (e.g., AVE7688), anti-transforming growth factor-β1 antibody, chemokine receptor 1 blockers, bone morphogenetic protein-7, PPARγ agonists (e.g., rosiglitazone, pioglitazone, MRL24, Fmoc-L-Leu, SR1664, SR1824, GW0072, MCC555, CLX-0921, PAT5A, L-764406, nTZDpa, CDDO (2-cyano-3,12-dioxooleana-1,9-dien-28-oic acid), ragaglitazar, O-arylmandelic acids, and NSAIDs) and/or BAY-12-9566, such that a synergistic effect in the prevention or treatment results.

In any case, the multiple therapeutic agents may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents.

EXAMPLES

The present technology is further illustrated by the following examples, which should not be construed as limiting in any way. For each of the examples below, any aromatic-cationic peptide described herein could be used. By way of example, but not by limitation, the aromatic-cationic peptide used in the example below could be 2'6'-Dmt-D-Arg-Phe-Lys-NH$_2$, Phe-D-Arg-Phe-Lys-NH$_2$, or D-Arg-2'6'-Dmt-Lys-Phe-NH$_2$ or any one or more of the peptides shown in Tables 6, 7, and/or 8.

Example 1—Use of Aromatic-Cationic Peptides in the Treatment of Alport Syndrome in Humans This example demonstrates the use of aromatic-cationic peptides, such as D-Arg-2',6'-Dmt-Lys-Phe-NH$_2$, or a pharmaceutically acceptable salt thereof, such as acetate, tartrate, or trifluoroacetate salt, in the treatment of Alport Syndrome.

Methods

Subjects suspected of having or diagnosed as having Alport Syndrome receive daily administrations of 1%, 5% or 10% solution of aromatic-cationic peptide, such as D-Arg-2',6'-Dmt-Lys-Phe-NH$_2$, or a pharmaceutically acceptable salt thereof, such as acetate, tartrate, or trifluoroacetate salt, alone or in combination with one or more additional therapeutic agents for the treatment or prevention of Alport Syndrome. Peptides and/or additional therapeutic agents are administered orally, topically, systemically, intravenously, subcutaneously, intraperitoneally, or intramuscularly according to methods known in the art. Subjects will be evaluated weekly for the presence and/or severity of signs and symptoms associated with Alport Syndrome, including, but not limited to, e.g., hematuria, proteinuria, cylindruria, leukocyturia, hypertension, edema, microalbuminuria, declining glomerular filtration rate, interstitial fibrosis, interstitial inflammation, tubular damage, GBM ultrastructural abnormalities, nephrotic syndrome, glomerulonephritis, end-stage kidney disease, chronic anemia, macrothrombocytopenia, osteodystrophy, sensorineural deafness, anterior lenticonus, dot-and-fleck retinopathy, posterior polymorphous corneal dystrophy, recurrent corneal erosion, temporal macular thinning, cataracts, lacrimation, photophobia, vision loss, keratoconus, and leiomyomatosis. Treatments are maintained until such a time as one or more signs or symptoms of Alport Syndrome are ameliorated or eliminated.

Results

It is predicted that subjects suspected of having or diagnosed as having Alport Syndrome and receiving therapeutically effective amounts of aromatic-cationic peptide, such as D-Arg-2',6'-Dmt-Lys-Phe-NH$_2$, or a pharmaceutically acceptable salt thereof, such as acetate, tartrate, or trifluoroacetate salt will display reduced severity or elimination of symptoms associated with Alport Syndrome. It is also expected that Alport Syndrome subjects treated with the aromatic-cationic peptide will show normalization of one or more of ADAM8, fibronectin, myosin 10, MMP-2, MMP-9, and podocin urine levels by at least 10% compared to the untreated Alport Syndrome controls. It is further expected that administration of D-Arg-2',6'-Dmt-Lys-Phe-NH$_2$ in combination with one or more additional therapeutic agents will have synergistic effects in this regard compared to that observed in subjects treated with the aromatic-cationic peptides or the additional therapeutic agents alone.

These results will show that aromatic-cationic peptides, such as D-Arg-2',6'-Dmt-Lys-Phe-NH$_2$, or a pharmaceutically acceptable salt thereof, such as acetate, tartrate, or trifluoroacetate salt are useful in the treatment of Alport Syndrome. These results will show that aromatic-cationic peptides, such as D-Arg-2',6'-Dmt-Lys-Phe-NH$_2$, or a pharmaceutically acceptable salt thereof, such as acetate, tartrate, or trifluoroacetate salt are useful in ameliorating one or more of the following symptoms: hematuria, proteinuria, cylindruria, leukocyturia, hypertension, edema, microalbuminuria, declining glomerular filtration rate, interstitial fibrosis, interstitial inflammation, tubular damage, GBM ultrastructural abnormalities, nephrotic syndrome, glomerulonephritis, end-stage kidney disease, chronic anemia, macrothrombocytopenia, osteodystrophy, sensorineural deafness, anterior lenticonus, dot-and-fleck retinopathy, posterior polymorphous corneal dystrophy, recurrent corneal erosion, temporal macular thinning, cataracts, lacrimation, photophobia, vision loss, keratoconus, and leiomyomatosis. Accordingly, the peptides are useful in methods comprising administering aromatic-cationic peptides to a subject in need thereof for the treatment of Alport Syndrome.

Example 2—Use of Aromatic-Cationic Peptides in the Prevention of Alport Syndrome in Humans This example demonstrates the use of aromatic-cationic peptides, such as D-Arg-2',6'-Dmt-Lys-Phe-NH$_2$, or a pharmaceutically acceptable salt thereof, such as acetate, tartrate, or trifluoroacetate salt, in the prevention of Alport Syndrome.
Methods
Subjects at risk of having Alport Syndrome receive daily administrations of 1%, 5% or 10% solution of aromatic-cationic peptide, such as D-Arg-2',6'-Dmt-Lys-Phe-NH$_2$, or a pharmaceutically acceptable salt thereof, such as acetate, tartrate, or trifluoroacetate salt, alone or in combination with one or more additional therapeutic agents for the treatment or prevention of Alport Syndrome. Peptides and/or additional therapeutic agents are administered orally, topically, systemically, intravenously, subcutaneously, intraperitoneally, or intramuscularly according to methods known in the art. Subjects will be evaluated weekly for the presence and/or severity of signs and symptoms associated with Alport Syndrome, including, but not limited to, e.g., hematuria, proteinuria, cylindruria, leukocyturia, hypertension, edema, microalbuminuria, declining glomerular filtration rate, interstitial fibrosis, interstitial inflammation, tubular damage, GBM ultrastructural abnormalities, nephrotic syndrome, glomerulonephritis, end-stage kidney disease, chronic anemia, macrothrombocytopenia, osteodystrophy, sensorineural deafness, anterior lenticonus, dot-and-fleck retinopathy, posterior polymorphous corneal dystrophy, recurrent corneal erosion, temporal macular thinning, cataracts, lacrimation, photophobia, vision loss, keratoconus, and leiomyomatosis.
Results
It is predicted that subjects at risk of having or diagnosed as having Alport Syndrome and receiving therapeutically effective amounts of aromatic-cationic peptide, such as D-Arg-2',6'-Dmt-Lys-Phe-NH$_2$, or a pharmaceutically acceptable salt thereof, such as acetate, tartrate, or trifluoroacetate salt will display delayed onset of Alport Syndrome, or prevention of onset of Alport Syndrome. It is also expected that the urine levels of one or more of ADAM8, fibronectin, myosin 10, MMP-2, MMP-9, and podocin in Alport Syndrome subjects treated with the aromatic-cationic peptide will resemble healthy controls. It is further expected that administration of D-Arg-2',6'-Dmt-Lys-Phe-NH$_2$ in combination with one or more additional therapeutic agents will have synergistic effects in this regard compared to that observed in subjects treated with aromatic-cationic peptides or the additional therapeutic agents alone.

These results will show that aromatic-cationic peptides, such as D-Arg-2',6'-Dmt-Lys-Phe-NH$_2$, or a pharmaceutically acceptable salt thereof, such as acetate, tartrate, or trifluoroacetate salt are useful in the prevention of Alport Syndrome. These results will show that aromatic-cationic peptides, such as D-Arg-2',6'-Dmt-Lys-Phe-NH$_2$, or a pharmaceutically acceptable salt thereof, such as acetate, tartrate, or trifluoroacetate salt are useful in preventing or delaying the onset of one or more of the following symptoms: hematuria, proteinuria, cylindruria, leukocyturia, hypertension, edema, microalbuminuria, declining glomerular filtration rate, interstitial fibrosis, interstitial inflammation, tubular damage, GBM ultrastructural abnormalities, nephrotic syndrome, glomerulonephritis, end-stage kidney disease, chronic anemia, macrothrombocytopenia, osteodystrophy, sensorineural deafness, anterior lenticonus, dot-and-fleck retinopathy, posterior polymorphous corneal dystrophy, recurrent corneal erosion, temporal macular thinning, cataracts, lacrimation, photophobia, vision loss, keratoconus, and leiomyomatosis.

Accordingly, the peptides are useful in methods comprising administering aromatic-cationic peptides to a subject in need thereof for the prevention of Alport Syndrome.

Example 3—Use of Aromatic-Cationic Peptides in the Treatment of Alport Syndrome in a Mouse Model This Example demonstrates the in vivo efficacy of aromatic-cationic peptides, such as D-Arg-2',6'-Dmt-Lys-Phe-NH$_2$, or a pharmaceutically acceptable salt thereof, such as acetate, tartrate, or trifluoroacetate salt, in treating Alport Syndrome in a mouse model.
Methods
Homozygous male Col4a3 null mice and wild-type litter mates were used in this study. Subjects were divided into the following groups:
 (1) Healthy wild-type controls
 (2) Col4a3 null mice treated with water
 (3) Col4a3 null mice treated with 1 mg/kg D-Arg-2'6'-Dmt-Lys-Phe-NH$_2$
 (4) Col4a3 null mice treated with 5 mg/kg D-Arg-2'6'-Dmt-Lys-Phe-NH$_2$
 (5) Col4a3 null mice treated with 5 mg/kg D-Arg-2'6'-Dmt-Lys-Phe-NH$_2$ (Pharmacokinetics group)

FIG. 2 illustrates the general protocol for the Alport Syndrome study. D-Arg-2',6'-Dmt-Lys-Phe-NH$_2$ was formulated in water and administered once daily by subcutaneous bolus injection at either 1 or 5 mg/kg starting from 5 weeks of age. Groups (1)-(4) consisted of 16 mice, out of which 10 were used for survival rate studies and 6 for pathology and RNA/protein analysis. Group (5) consisted of 6 mice, 3 of which were sacrificed at 30 minutes after the 7th injection (age, 6 weeks), and 3 at 24 hours after the 7th injection (age, 6 weeks).

Urine and blood (serum) samples were collected every 2 weeks at week 5, 7, 9, 11, 13, and 15.

Six animals from experimental groups (1)-(4) were sacrificed for tissue collection at week 15. One kidney from each animal was harvested for protein/RNA analysis and the second kidney was collected for paraffin sections for analysis via microscopy. Survival data was collected for the remaining 10 animals in groups (1)-(4).

Renal Histology:

For light microscopy, a subset of kidneys from each group (n=3) was fixed in 4% paraformaldehyde, embedded in paraffin, and cut into sections. Three-micron sections were stained with Hematoxylin and Eosin stain (H&E stain) or periodic acid-Schiff reagent to assess overall pathology scores with respect to glomeruli damage, tubular damage, interstitial inflammation and interstitial fibrosis.

Renal Function:

Renal function was assessed by measuring blood urea nitrogen (BUN) and Urine albumin/Creatine ratio (ACR).

Analysis of Mitochondrial Pathways:

Kidneys were removed, immersed in OCT, and snap-frozen in liquid nitrogen vapor. Five-micrometer cryostat sections were placed on slides and postfixed in acetone. Tissues were immunostained with antibodies to Drp1, Mfn1, OPA1 and Txn2 proteins using standard techniques known in the art. Additionally, the mRNA expression levels of SOD1 and SOD2 were analyzed via q-RT-PCR.

Results

Figure 3A:
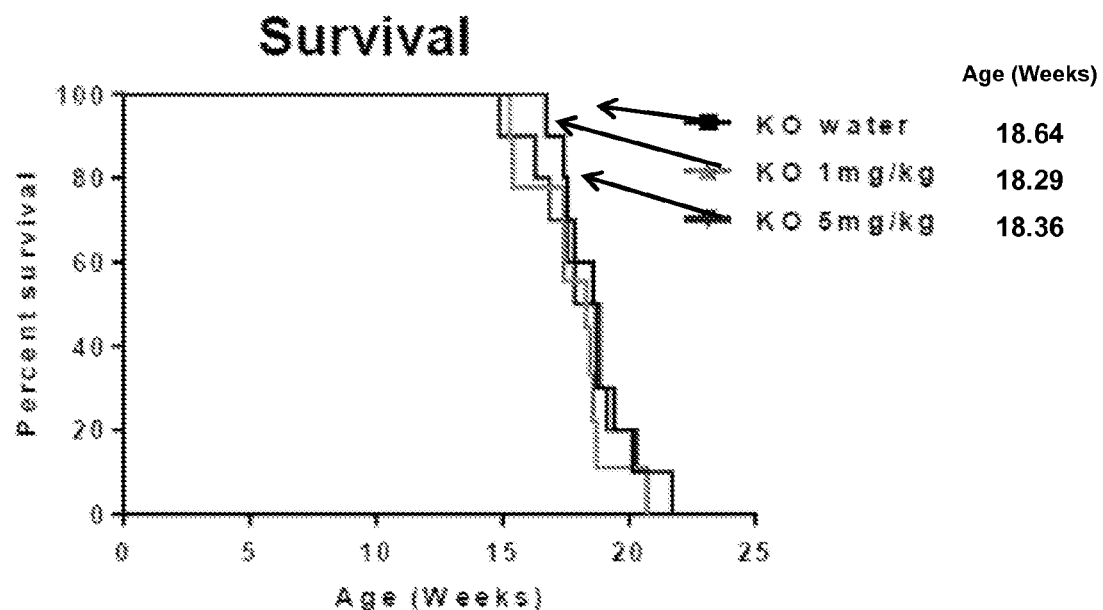
FIG. 3A shows the survival curves of Col4a3 null mice treated with water, 1 mg/kg D-Arg-2',6'-Dmt-Lys-Phe-NH₂, and 5 mg/kg D-Arg-2',6'-Dmt-Lys-Phe-NH₂.
Figure 3B:
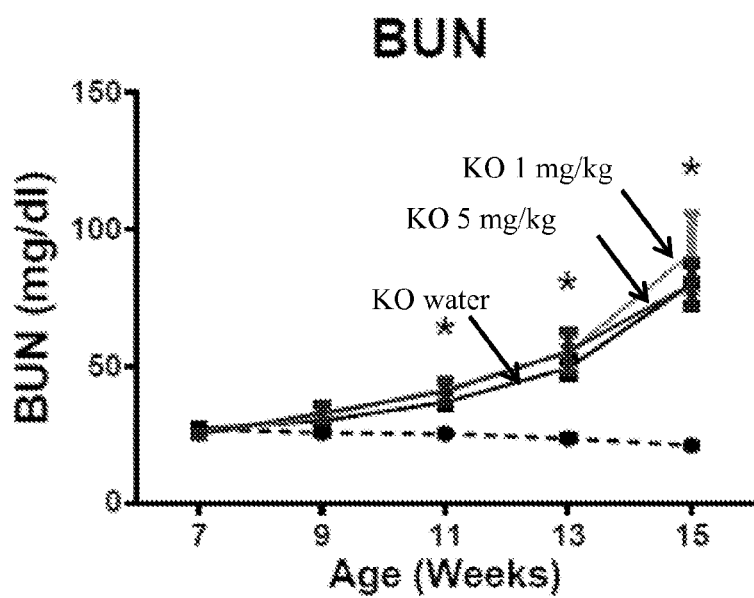
FIG. 3B shows BUN levels of Col4a3 null mice treated with water, 1 mg/kg D-Arg-2',6'-Dmt-Lys-Phe-NH₂, and 5 mg/kg D-Arg-2',6'-Dmt-Lys-Phe-NH₂ between 7 weeks of age and 15 weeks of age.
Figure 3C:
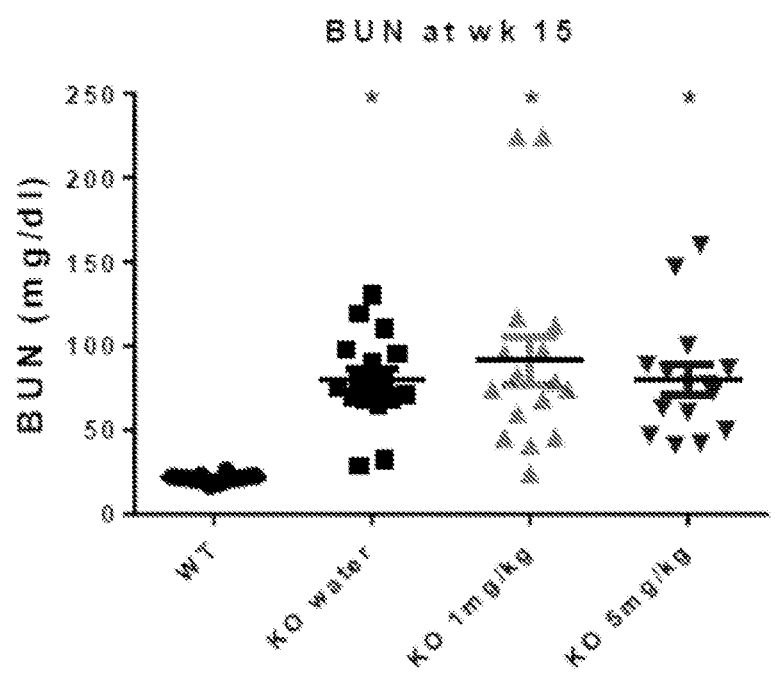
FIG. 3C shows the BUN levels of Col4a3 null mice treated with water, 1 mg/kg D-Arg-2',6'-Dmt-Lys-Phe-NH₂, and 5 mg/kg D-Arg-2',6'-Dmt-Lys-Phe-NH₂ at 15 weeks of age relative to wild-type mice.

As shown in FIG. 3A, treatment with 1 mg/kg or 5 mg/kg D-Arg-2'6'-Dmt-Lys-Phe-NH$_2$ did not impact the survival rate of Col4a3 null mice (Alport mice); peptide administration was not harmful. The BUN levels of untreated Col4a3 null mice (Alport mice) progressively increased between 7 weeks of age and 15 weeks of age compared to wild-type mice (FIG. 3B). Treatment with 1 mg/kg or 5 mg/kg D-Arg-2'6'-Dmt-Lys-Phe-NH$_2$ did not impact the BUN levels in Col4a3 null mice (Alport mice) at 15 weeks of age. See FIGS. 3B and 3C.

Figure 4A:
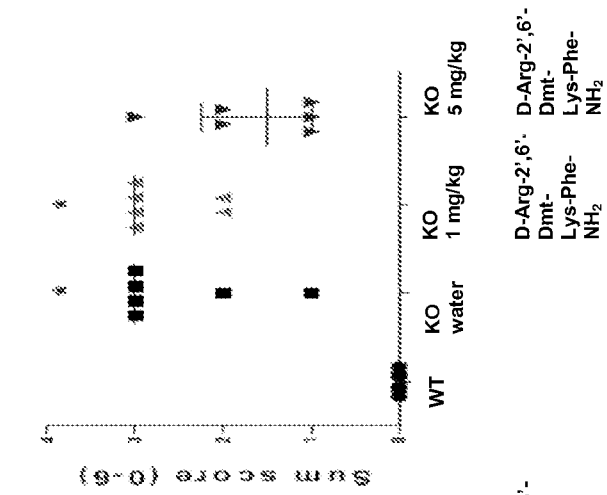
FIG. 4A shows the tubule pathology scores (indicative of tubular damage) of Col4a3 null mice treated with water, 1 mg/kg D-Arg-2',6'-Dmt-Lys-Phe-NH₂, and 5 mg/kg D-Arg-2',6'-Dmt-Lys-Phe-NH₂ at 15 weeks of age relative to wild-type mice.
Figure 4B:
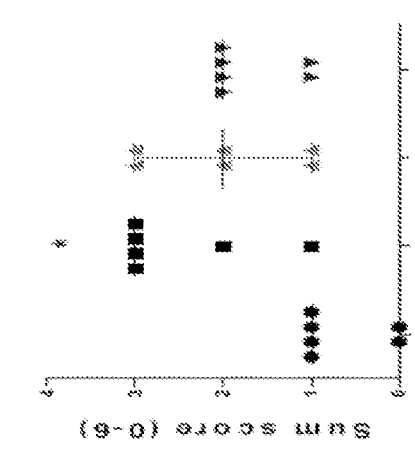
FIG. 4B shows the interstitial inflammation scores of Col4a3 null mice treated with water, 1 mg/kg D-Arg-2',6'-Dmt-Lys-Phe-NH₂, and 5 mg/kg D-Arg-2',6'-Dmt-Lys-Phe-NH₂ at 15 weeks of age relative to wild-type mice.
Figure 4C:
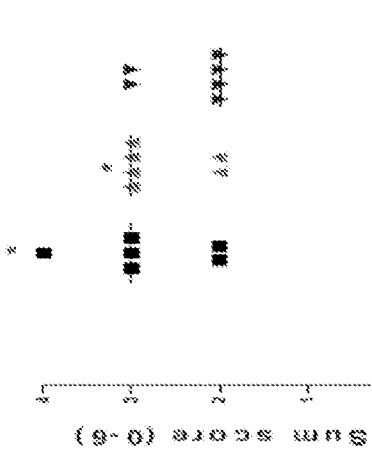
FIG. 4C shows the interstitial fibrosis scores of Col4a3 null mice treated with water, 1 mg/kg D-Arg-2',6'-Dmt-Lys-Phe-NH₂, and 5 mg/kg D-Arg-2',6'-Dmt-Lys-Phe-NH₂ at 15 weeks of age relative to wild-type mice.

As shown in FIGS. 4A-4C, untreated Col4a3 null mice (Alport mice) exhibited tubular damage, interstitial inflammation, and interstitial fibrosis compared to wild-type controls. FIGS. 4A-4C demonstrate that Col4a3 null mice receiving 5 mg/kg D-Arg-2',6'-Dmt-Lys-Phe-NH$_2$ showed a reduction in the severity of tubular damage, interstitial inflammation, and interstitial fibrosis. For instance, 66% (4/6) of untreated Col4a3 null mice (Alport mice) exhibited a tubule pathology score of 3 and higher, whereas only 33% (2/6) of Col4a3 null mice (Alport mice) treated with 5 mg/kg D-Arg-2',6'-Dmt-Lys-Phe-NH$_2$ exhibited the same scores. See FIG. 4A. According to FIG. 4B, 66% (4/6) of untreated Col4a3 null mice (Alport mice) exhibited an interstitial inflammation severity score of 3. In contrast, none of the Col4a3 null mice (Alport mice) treated with 5 mg/kg D-Arg-2',6'-Dmt-Lys-Phe-NH$_2$ exhibited the same severity of interstitial inflammation (0/6 had an interstitial inflammation severity score of 3). FIG. 4C shows that 66% (4/6) of untreated Col4a3 null mice (Alport mice) exhibited an interstitial fibrosis severity score of 3, whereas only 17% (1/6) of Col4a3 null mice (Alport mice) treated with 5 mg/kg D-Arg-2',6'-Dmt-Lys-Phe-NH$_2$ exhibited the same severity score for interstitial fibrosis.

Figure 5A:
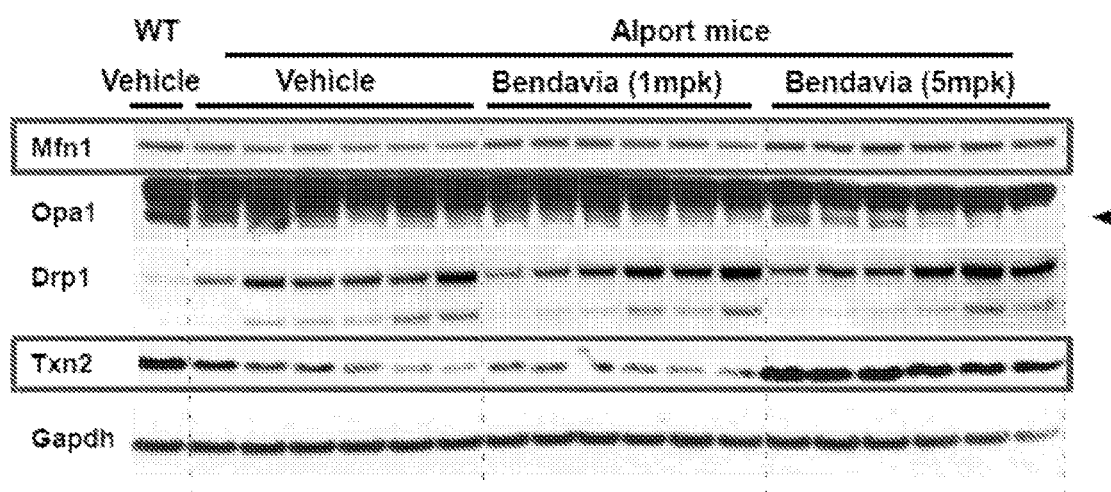
FIG. 5A shows the protein expression levels of Mfn1, Opa1, Drp1 and Txn2 in Col4a3 null mice treated with water, 1 mg/kg D-Arg-2',6'-Dmt-Lys-Phe-NH₂, and 5 mg/kg D-Arg-2',6'-Dmt-Lys-Phe-NH₂ at 15 weeks of age relative to wild-type mice.
Figure 5B:
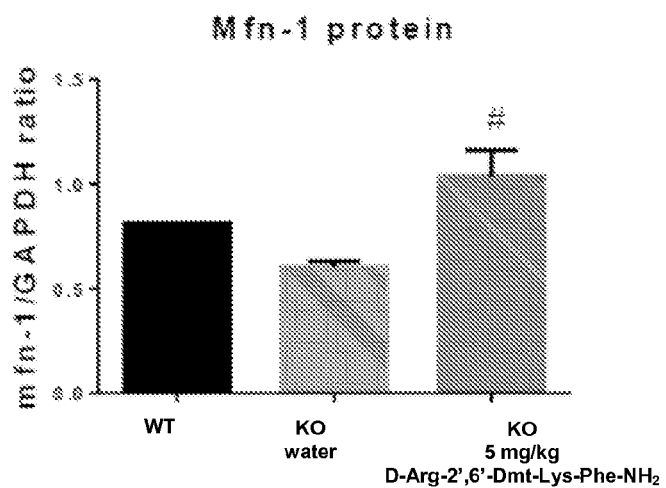
FIG. 5B shows the quantification of MFN 1 protein expression levels relative to control GADPH levels in Col4a3 null mice treated with water, and 5 mg/kg D-Arg-2',6'-Dmt-Lys-Phe-NH₂ at 15 weeks of age relative to wild-type mice.
Figure 5C:
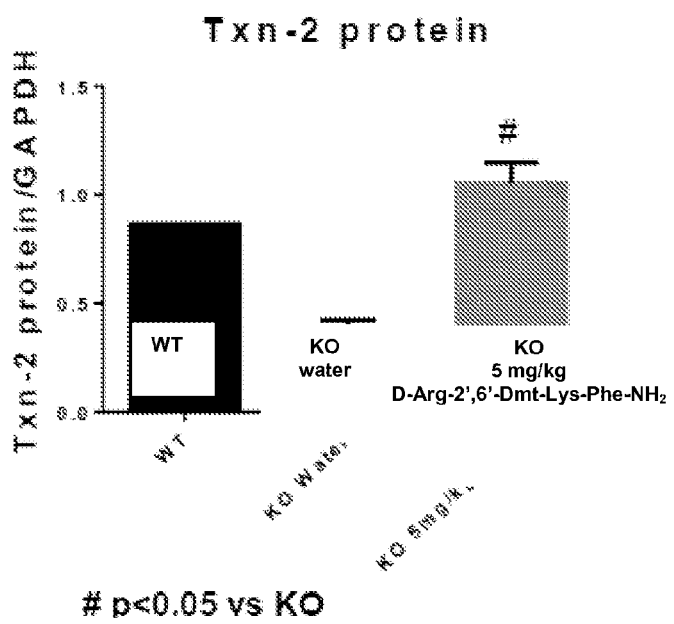
FIG. 5C shows the quantification of TXN2 protein expression levels relative to control GADPH levels in Col4a3 null mice treated with water, and 5 mg/kg D-Arg-2',6'-Dmt-Lys-Phe-NH₂ at 15 weeks of age relative to wild-type mice.

FIGS. 5A-5C demonstrate that treatment with 5 mg/kg D-Arg-2',6'-Dmt-Lys-Phe-NH$_2$ significantly elevates the expression of Mfn1 and Txn2 in Col4a3 null mice (Alport mice) compared to untreated Col4a3 null mice (Alport mice).

Figure 6A:
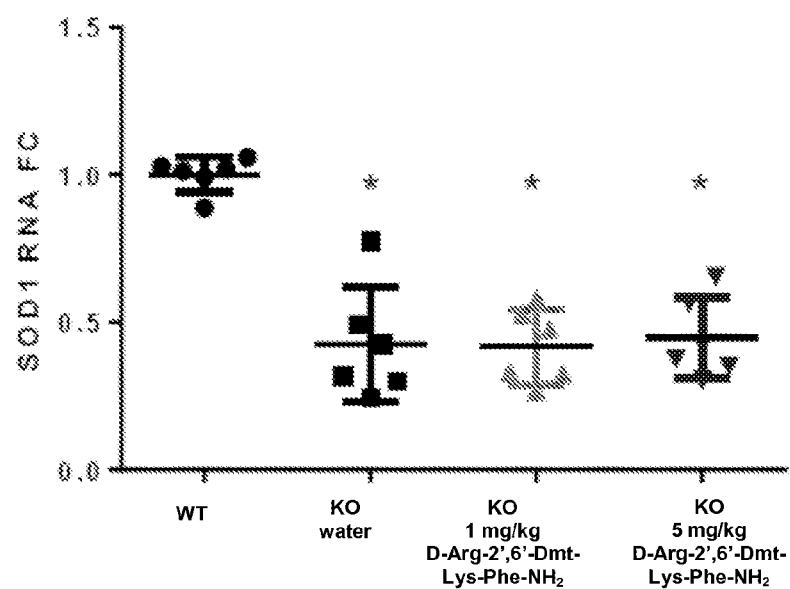
FIG. 6A shows SOD1 mRNA expression levels in Col4a3 null mice treated with water, 1 mg/kg D-Arg-2',6'-Dmt-Lys-Phe-NH₂, and 5 mg/kg D-Arg-2',6'-Dmt-Lys-Phe-NH₂ at 15 weeks of age relative to wild-type mice.
Figure 6B:
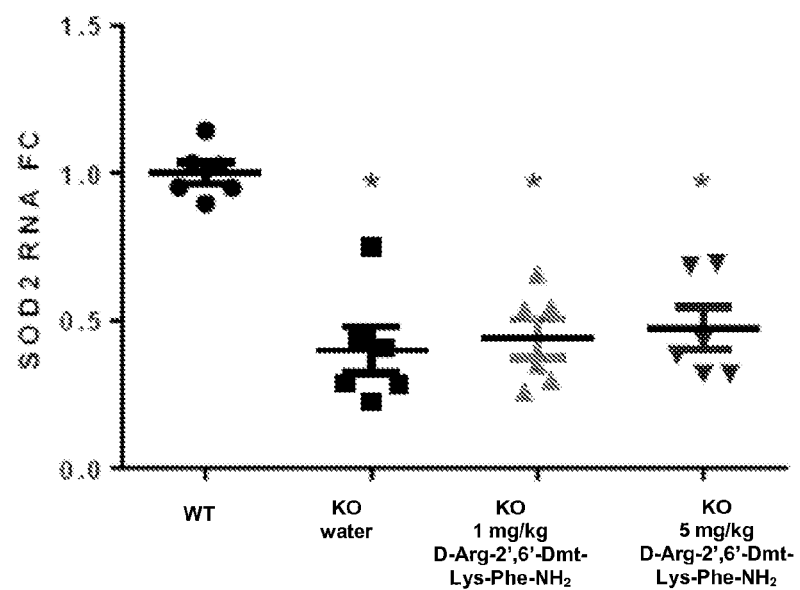
FIG. 6B shows SOD2 mRNA expression levels in Col4a3 null mice treated with water, 1 mg/kg D-Arg-2',6'-Dmt-Lys-Phe-NH₂, and 5 mg/kg D-Arg-2',6'-Dmt-Lys-Phe-NH₂ at 15 weeks of age relative to wild-type mice.

As shown in FIGS. 6A and 6B, untreated Col4a3 null mice (Alport mice) exhibit a significant reduction in SOD1 and SOD2 mRNA expression compared to wild-type controls. Treatment with 1 mg/kg or 5 mg/kg D-Arg-2'6'-Dmt-Lys-Phe-NH$_2$ failed to rescue the reduced SOD1 and SOD2 mRNA expression levels observed in Col4a3 null mice (Alport mice). See FIGS. 6A and 6B.

Figure 7:
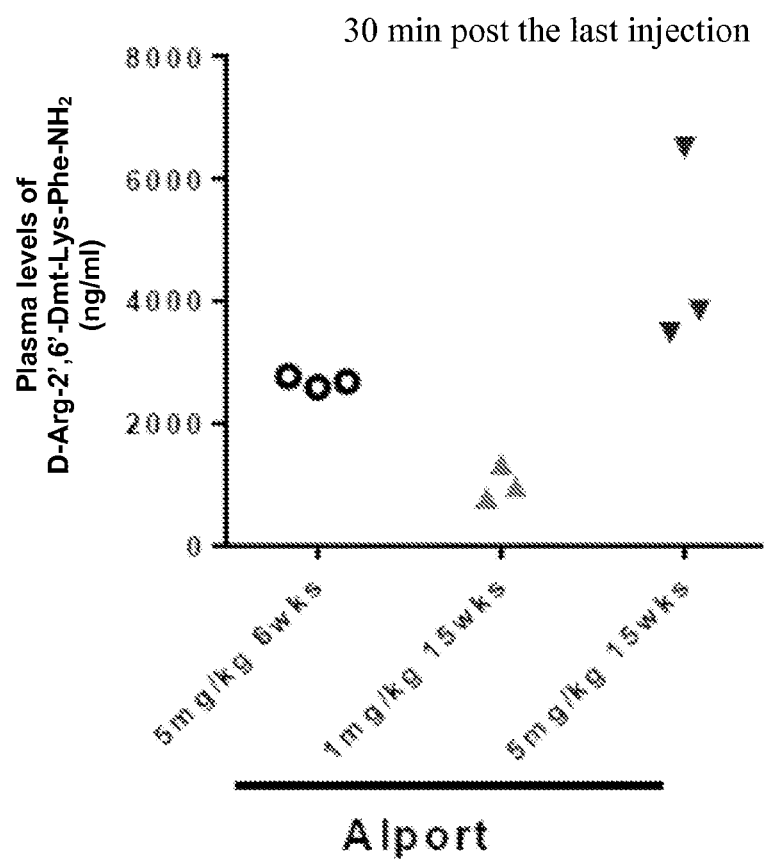
FIG. 7 shows the D-Arg-2',6'-Dmt-Lys-Phe-NH₂ plasma levels in Col4a3 null mice treated with (a) 5 mg/kg D-Arg-2',6'-Dmt-Lys-Phe-NH₂ at 6 weeks of age (group (5)), (b) 1 mg/kg D-Arg-2',6'-Dmt-Lys-Phe-NH₂ at 15 weeks of age, and (c) 5 mg/kg D-Arg-2',6'-Dmt-Lys-Phe-NH₂ at 15 weeks of age. D-Arg-2',6'-Dmt-Lys-Phe-NH₂ plasma levels were assessed 30 minutes after the last injection.

FIG. 7 shows D-Arg-2',6'-Dmt-Lys-Phe-NH$_2$ plasma levels in Col4a3 null mice (Alport mice) treated with (a) 5 mg/kg D-Arg-2',6'-Dmt-Lys-Phe-NH$_2$ at 6 weeks of age, (b) 1 mg/kg D-Arg-2',6'-Dmt-Lys-Phe-NH$_2$ at 15 weeks of age, and (c) 5 mg/kg D-Arg-2',6'-Dmt-Lys-Phe-NH$_2$ at 15 weeks of age. D-Arg-2',6'-Dmt-Lys-Phe-NH$_2$ plasma levels were assessed 30 minutes after the last injection. Col4a3 null mice (Alport mice) that received daily injections of 5 mg/kg D-Arg-2',6'-Dmt-Lys-Phe-NH$_2$ at 15 weeks of age showed the highest D-Arg-2',6'-Dmt-Lys-Phe-NH$_2$ plasma levels. See FIG. 7.

These results show that aromatic-cationic peptides, such as D-Arg-2',6'-Dmt-Lys-Phe-NH$_2$, or a pharmaceutically acceptable salt thereof, such as acetate, tartrate, or trifluoroacetate salt are useful in treating Alport Syndrome. These results also demonstrate that aromatic-cationic peptides, such as D-Arg-2',6'-Dmt-Lys-Phe-NH$_2$, or a pharmaceutically acceptable salt thereof, such as acetate, tartrate, or trifluoroacetate salt are useful in ameliorating the severity of tubular damage, interstitial inflammation and interstitial fibrosis in subjects that are at risk of developing Alport Syndrome.

Accordingly, the aromatic-cationic peptides of the present technology are useful in methods comprising administering aromatic-cationic peptides to a subject in need thereof for the treatment of Alport Syndrome.

Example 4—Use of Aromatic-Cationic Peptides in the Treatment of a Condition Characterized by Decreased Expression of Col4a4 and Col4a5

This Example will demonstrates the in vivo efficacy of aromatic-cationic peptides, such as D-Arg-2',6'-Dmt-Lys-Phe-NH$_2$, or a pharmaceutically acceptable salt thereof, such as acetate, tartrate, or trifluoroacetate salt, in treating deficiency of COLA4A4 and COLA4A5 expression in mouse models.

Methods

Homozygous male mice having decreased expression of either Col4a4 or Col4a5 and wild-type litter mates will be used in this study. Subjects will be divided into the following groups:

(1) Healthy wild-type controls
(2) Col4a4 and Col4a5 deficient mice treated with water
(3) Col4a4 and Col4a5 deficient mice treated with 1 mg/kg D-Arg-2'6'-Dmt-Lys-Phe-NH$_2$
(4) Col4a4 and Col4a5 deficient mice treated with 5 mg/kg D-Arg-2'6'-Dmt-Lys-Phe-NH$_2$
(5) Col4a4 and Col4a5 deficient mice treated with 5 mg/kg D-Arg-2'6'-Dmt-Lys-Phe-NH$_2$ (Pharmacokinetics group)

D-Arg-2',6'-Dmt-Lys-Phe-NH$_2$ will be formulated in water and administered once daily by subcutaneous bolus injection at either 1 or 5 mg/kg starting from 5 weeks of age. Groups (1)-(4) will include 16 mice, out of which 10 will be used for survival rate studies and 6 for pathology and RNA/protein analysis. Group (5) will include 6 mice, 3 of which will be sacrificed at 30 minutes after the 7th injection (age, 6 weeks), and 3 at 24 hours after the 7th injection (age, 6 weeks).

Urine and blood (serum) samples will be collected every 2 weeks at week 5, 7, 9, 11, 13, and 15.

Six animals from experimental groups (1)-(4) will be sacrificed for tissue collection at week 15. One kidney from each animal will be harvested for protein/RNA analysis and the second kidney will be collected for paraffin sections for analysis via microscopy. Survival data will be collected for the remaining 10 animals in groups (1)-(4).

Renal Histology:

For light microscopy, a subset of kidneys from each group (n=3) will be fixed in 4% paraformaldehyde, embedded in paraffin, and cut into sections. Three-micron sections will be stained with Hematoxylin and Eosin stain (H&E stain) or periodic acid-Schiff reagent to assess overall pathology scores with respect to glomeruli damage, tubular damage, interstitial inflammation and interstitial fibrosis.

Renal Function:

Renal function will be assessed by measuring blood urea nitrogen (BUN) and Urine albumin/Creatine ratio (ACR).

Analysis of Mitochondrial Pathways:

Kidneys will be removed, immersed in OCT, and snap-frozen in liquid nitrogen vapor. Five-micrometer cryostat sections will be placed on slides and postfixed in acetone. Tissues will be immunostained with antibodies to Drp1, Mfn1, OPA1 and Txn2 proteins using standard techniques known in the art. Additionally, the mRNA expression levels of SOD1 and SOD2 will be analyzed via q-RT-PCR.

Results

It is anticipated that these results will show that aromatic-cationic peptides, such as D-Arg-2',6'-Dmt-Lys-Phe-NH$_2$, or a pharmaceutically acceptable salt thereof, such as acetate, tartrate, or trifluoroacetate salt are useful in treating a disease or condition one or more of COL4A3, COL4A4 and COL4A5 genes. These results will also demonstrate that aromatic-cationic peptides, such as D-Arg-2',6'-Dmt-Lys-Phe-NH$_2$, or a pharmaceutically acceptable salt thereof, such as acetate, tartrate, or trifluoroacetate salt are useful in ameliorating the severity of one or more of collagen deformation and/or irregularities, tubular damage, interstitial inflammation and/or interstitial fibrosis in subjects that are at risk of developing a disease or condition characterized by a reduction of function, decreased expression level of, and/or deficiency in one or more of COL4A3, COL4A4 and COL4A5 genes.

Accordingly, the aromatic-cationic peptides of the present technology are useful in methods comprising administering aromatic-cationic peptides to a subject in need thereof for the treatment of a disease or condition characterized by a reduction of function, decreased expression level of, and/or deficiency in one or more of COL4A3, COL4A4 and COL4A5 genes.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

What is claimed is:

1. A method for treating a disease or condition characterized by a reduction of function, decreased expression levels of, or a deficiency in the COL4A3 gene in a subject in need thereof, comprising: administering to the subject a therapeutically effective amount of the aromatic-cationic peptide D-Arg-2',6'-Dmt-Lys-Phe-NH$_2$ or a pharmaceutically acceptable salt thereof.

2. The method of claim 1, wherein the pharmaceutically acceptable salt comprises acetate, tartrate, or trifluoroacetate salt.

3. The method of claim 1, wherein the disease or condition is characterized by a reduction of function in COL4A3 compared to a normal control subject.

4. The method of claim 1, wherein the disease or condition is characterized by a deficiency in COL4A3 compared to a normal control subject.

5. The method of claim 1, wherein the disease or condition is characterized by decreased expression levels of COL4A3 compared to a normal control subject.

6. The method of claim 1, wherein the subject is human.

7. The method of claim 1, wherein peptide treatment results in elevated Mfn1 expression and/or function compared to an untreated subject having said disease or condition.

8. The method of claim 1, wherein the aromatic-cationic peptide is administered orally, topically, intranasally, systemically, intravenously, subcutaneously, intraperitoneally, intradermally, intraocularly, iontophoretically, transmucosally, or intramuscularly.

9. The method of claim 1, wherein the peptide is administered daily for 6 weeks or more.

10. The method of claim 1, wherein the peptide is administered daily for 12 weeks or more.

11. The method of claim 1, further comprising separately, sequentially or simultaneously administering one or more additional therapeutic agents to the subject.

12. The method of claim 11, wherein the additional therapeutic agents are selected from the group consisting of: angiotensin II converting enzyme inhibitors (ACE inhibitors), angiotensin II receptor blockers (ARBs), HMG-CoA reductase inhibitors, aldosterone inhibitors, aliskiren, calcineurin inhibitors, endothelin receptor antagonists sulodexide, vasopeptidase inhibitors, anti-transforming growth factor-$\beta$1 antibody, chemokine receptor 1 blockers, bone morphogenetic protein-7, PPAR$\gamma$ agonists, and BAY-12-9566.

* * * * *